(12) United States Patent
Joo et al.

(10) Patent No.: US 8,158,327 B2
(45) Date of Patent: Apr. 17, 2012

(54) ONIUM SALT COMPOUND, POLYMER COMPOUND COMPRISING THE SALT COMPOUND, CHEMICALLY AMPLIFIED RESIST COMPOSITION COMPRISING THE POLYMER COMPOUND, AND METHOD FOR PATTERNING USING THE COMPOSITION

(75) Inventors: Hyun-Sang Joo, Daejeongwangyeok-si (KR); Joo-Hyeon Park, Cheonan-si (KR); Jung-Hoon Oh, Cheonan-si (KR); Dae-Hyeon Shin, Seoul (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 633 days.

(21) Appl. No.: 12/321,111

(22) Filed: Jan. 15, 2009

(65) Prior Publication Data

US 2010/0075256 A1    Mar. 25, 2010

(30) Foreign Application Priority Data

Sep. 23, 2008    (KR) .................. 10-2008-0093299

(51) Int. Cl.
G03F 7/004    (2006.01)
G03F 7/30    (2006.01)
C08F 228/02    (2006.01)

(52) U.S. Cl. ............ 430/270.1; 430/326; 430/330; 430/905; 430/910; 526/287

(58) Field of Classification Search .......... 430/270.1, 430/326, 330, 905, 910; 526/287
See application file for complete search history.

(56) References Cited

U.S. PATENT DOCUMENTS

2007/0149702 A1*    6/2007    Ando et al. ................. 524/556
* cited by examiner

*Primary Examiner* — John Chu
(74) *Attorney, Agent, or Firm* — Davidson, Davidson & Kappel, LLC

(57) ABSTRACT

A compound represented by the following formula (1) is provided:

[Formula 1]

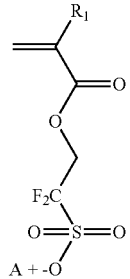

wherein $R_1$ represents a hydrogen atom, a trifluoromethyl group, an alkyl group, or an alkoxy group; and A represents a group represented by the following formula (2) or formula (3):

[Formula 2]

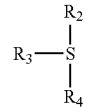

[Formula 3]

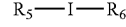

wherein $R_2$, $R_3$, $R_4$, $R_5$ and $R_6$ each independently represent a substituted or unsubstituted alkyl group, a substituted or unsubstituted allyl group, a substituted or unsubstituted perfluoroalkyl group, a substituted or unsubstituted benzyl group, or a substituted or unsubstituted aryl group; and two or more of $R_2$, $R_3$ and $R_4$ may be linked to each other to form a saturated or unsaturated carbon ring or a saturated or unsaturated heterocyclic ring.

The chemically amplified resist composition comprising a polymer compound which is produced from the compound of formula 1 according to the present invention provides a chemically amplified resist sensitive to far-ultraviolet radiation, which is represented by KrF excimer laser or ArF excimer laser.

16 Claims, 16 Drawing Sheets

Kumho Petrochemical Co.,Ltd
*GPC Characterization*

Identification: OT-18[Solid]
File Name: OT-18!!

< Run Conditions >

System: DM400+External RI
Columns: G4000Hhr+G2500Hhr
Solvent: THF
Flow Rate: 1.000 mL/min
Concentration: 0.000 mg/mL
Inj. Vol.: 100.0 uL
Analyst: Hong Yong Hwa

< GPC Data Summary >

Mn: 760    Pd: 1.57
Mw: 1,190  MP: 900
Mz: 1,760
% Below 1,000:   100.0
% Above 20,000:    0.0

Kumho Petrochemical Co.,Ltd
*GPC Characterization*

Identification: OT-19[Solid]
File Name: OT-19!

< Run Conditions >

System: DM400+External RI
Columns: G4000Hhr+G2500Hhr
Solvent: THF
Flow Rate: 1.000 mL/min
Concentration: 0.000 mg/mL
Inj. Vol.: 100.0 uL
Analyst: Hong Yong Hwa

< GPC Data Summary >

Mn: 800      Pd: 1.54
Mw: 1,230    MP: 920
Mz: 1,800
% Below 1,000:     100.0
% Above 20,000:    0.0

Kumho Petrochemical Co.,Ltd
*GPC Characterization*

Identification: OT-20[Solid]
File Name: OT-20!

< Run Conditions >

System: DM400+External RI
Columns: G4000Hhr+G2500Hhr
Solvent: THF
Flow Rate: 1.000 mL/min
Concentration: 0.000 mg/mL
Inj. Vol.: 100.0 uL
Analyst: Hong Yong Hwa < GPC Data Summary >

| Mn: 950 | Pd: 1.27 |
| --- | --- |
| Mw: 1,210 | MP: 990 |
| Mz: 1,530 | |
| % Below 1,000: | 100.0 |
| % Above 20,000: | 0.0 |

Kumho Petrochemical Co.,Ltd
*GPC Characterization*

Identification: OT-21[Solid]
File Name: OT-21!

< Run Conditions >

System: DM400+External RI
Columns: G4000Hhr+G2500Hhr
Solvent: THF
Flow Rate: 1.000 mL/min
Concentration: 0.000 mg/mL
Inj. Vol.: 100.0 uL
Analyst: Hong Yong Hwa < GPC Data Summary >

Mn: 740    Pd: 1.57
Mw: 1,160  MP: 980
Mz: 1,690
% Below 1,000:   100.0
% Above 20,000:    0.0

Kumho Petrochemical Co.,Ltd
*GPC Characterization*

Identification: OT-23[Solid]
File Name: OT-23!

< Run Conditions >

System: DM400+External RI
Columns: G4000Hhr+G2500Hhr
Solvent: THF
Flow Rate: 1.000 mL/min
Concentration: 0.000 mg/mL
Inj. Vol.: 100.0 uL
Analyst: Hong Yong Hwa < GPC Data Summary >

| | |
|---|---|
| Mn: 880 | Pd: 1.57 |
| Mw: 1,380 | MP: 1,090 |
| Mz: 1,990 | |
| % Below 1,000: | 100.0 |
| % Above 20,000: | 0.0 |

Kumho Petrochemical Co., Ltd
*GPC Characterization*

Identification: PBP
File Name: PBP

< Run Conditions >

System: DM400+External RI
Columns: G4000Hhr+G2500Hhr
Solvent: THF
Flow Rate: 1.000 mL/min
Concentration: 0.000 mg/mL
Inj. Vol.: 100.0 uL
Analyst: Hong Yong Hwa

< GPC Data Summary >

Mn: 1,060    Pd: 1.68
Mw: 1,780    MP: 1,810
Mz: 2,650
% Below 1,000:    100.0
% Above 20,000:    0.0

ONIUM SALT COMPOUND, POLYMER COMPOUND COMPRISING THE SALT COMPOUND, CHEMICALLY AMPLIFIED RESIST COMPOSITION COMPRISING THE POLYMER COMPOUND, AND METHOD FOR PATTERNING USING THE COMPOSITION

This application claims priority under 35 U.S.C. §119 from Korean Patent Application 10-2008-0093299, filed on Sep. 23, 2008, the contents of which are hereby incorporated by reference in their entirety for all purposes as if fully set forth herein.

BACKGROUND OF THE INVENTION

1. Field of the Invention

The present invention relates to a polymer compound having improved line edge roughness, resolution, adhesiveness to a substrate, thermal stability and the like as a result of inducing uniform distribution of acid, and a chemically amplified resist composition comprising the polymer compound. More particularly, the invention relates to a novel polymer compound which can be used in the production of a resist useful for microprocessing using various radiations far-ultraviolet radiation such as KrF excimer laser or ArF excimer laser, X-radiation such as synchrotron radiation, or charged particle radiation such as electron beam, and a resist composition comprising the polymer compound.

2. Description of the Related Art

Recently, as the semiconductor industry is undergoing a transition to technologies involving line widths of 50 nanometers or less, newer and more advanced lithographic technologies are anticipated to emerge. Although the technology of extreme ultraviolet (EUV) lithography may serve as one of those important technologies capable of patterning in such extreme ranges of line width, the technology of realizing a pattern with a line width of 32 nanometers or less must be a very elaborating operation. The 193-nm lithographic technology can be said to be an important means for realizing the technologies involving line widths around 32 nm in the future, and such technologies can be made possible if the numerical aperture (NA) is increased. According to Rayleigh's Equation, when the refractive index of an immersion fluid or immersion resist is increased, the numerical aperture can be increased as shown in the equation below, and at the same time, the resolution can also be increased. An increase in the refractive index may also bring about an increase in the DOF.

$$R=(K1 \cdot \lambda)/(NA), NA=n \sin \theta$$

wherein R=resolution, λ=wavelength, NA=numerical aperture, n=refractive index, and θ=incident angle.

There is an on-going demand for new resist materials for the purpose of improvements in the properties such as resolution, sensitivity, refractive index and line edge roughness. The refractive index of the currently used resists is in general about 1.65, but the refractive index has been increased to 1.75 or higher by introducing elements such as sulfur to polymers, and resist technologies exhibiting faster sensitivity have been reported. However, these results are somewhat not very satisfactory in the realization of semiconductor integrated circuits requiring further micronization, and in some cases, there also occurs a problem of the photospeed being slow.

In the case of a polymer used as the main raw material of resist, the polymer should have light absorption at the minimum level at the exposure wavelength. In addition to the resist for EUV, the chemically amplified resists which have been conventionally used for ArF excimer laser are in most cases formed from acrylic polymers as the main material, but the acrylic polymers have a disadvantage that the resistance to dry plasma etch is low due to large quantities of oxygen atoms present in the polymer. It is disadvantageous because if the etch resistance is low, the thickness of the resist pattern should be increased to complement for the low resistance, and as the thickness of the pattern is increased, the probability for the pattern to stand safely on the substrate without collapsing becomes lower.

In order to overcome such disadvantages, resins containing many alicyclic olefin groups have been developed as the polymer to be used in the resists for ArF excimer laser. For example, a (meth)acrylate polymer containing an isobornyl group or an adamantanyl group, an olefin polymer purely composed of a norbornene derivative, a maleic anhydride-cycloolefin polymer, and the like may be mentioned.

The (meth)acrylate polymer may be exemplified by the polymer containing an alicyclic functional group, which was published in SPIE 2724:334 (1996), while the maleic anhydride-cycloolefin polymer may be exemplified by the polymer published in SPIE 2724:355 (1996). The case of the (meth)acrylate polymer has less light absorption, but has a disadvantage of having poor etch resistance compared to aromatic compounds. The maleic anhydride-cycloolefin polymer has excellent etch resistance compared to (meth)acrylate polymers, but has a disadvantage that the polymer absorbs too much light in the ArF excimer laser region so that the perpendicularity of the pattern is deteriorated. Furthermore, maleic anhydride monomers have a disadvantage that the monomers undergo hydrolysis reaction due to the moisture in the atmosphere, and thus have poor storage stability when prepared into a resist and put under storage. On the other hand, polymerization of pure olefin derivatives have disadvantages that metallic catalysts should be used, and that the polymerized resins are so hard that the resins do not show excellent properties as resist materials.

In order to supplement these disadvantages described above, the recent trend is focused on the use of more advanced forms of (meth)acrylate copolymers in the resist compositions. In these polymers, alicyclic olefins having more carbon atoms are introduced into the main chain so as to further enhance the etch resistance compared to the polymers using (meth)acrylic derivatives of the early times, and acid-labile moieties do not all vaporize during soft baking, but remain in an oily state in the resist film and tend to facilitate the flow of the acid generated by a photoacid generator during exposure, to thereby improve the patterning properties. Examples of such copolymers include those described in Korean Unexamined Patent Application Nos. 10-2006-7002354 and 10-2004-0080060, Japanese Unexamined Patent Application Publication No. 2002-293840, and the like.

SUMMARY OF THE INVENTION

It is an object of the present invention to provide a chemically amplified resist composition which is responsive to KrF excimer laser, ArF excimer laser, X-ray or the like. In providing such a resist composition, there is a problem that various required properties must be satisfied in accordance with the functions of semiconductor integrated circuits which increasingly require finer line widths, and as one of the most essential characteristics required by fine patterns including the EUV lithographic patterns, there may be mentioned line edge roughness. Furthermore, among the various factors affecting the line edge roughness, uniform dispersion of a photoacid generator or various additives in the resist film may also be mentioned as the most essential characteristic.

In an attempt to solve the problems as described above, it is an aspect of the present invention to provide a chemically amplified resist composition having decreased line edge roughness and reduced amount of gas generation, and having characteristics such as high sensitivity and high thermal stability.

It is another aspect of the invention to provide a novel polymer compound containing a photoacid generator, which is used in the resist composition.

According to an embodiment of the present invention, there is provided a compound represented by the following formula (1):

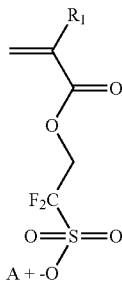

[Formula 1]

wherein $R_1$ represents a hydrogen atom, a trifluoromethyl group, an alkyl group having 1 to 5 carbon atoms, or an alkoxy group having 1 to 5 carbon atoms; and A represents a group represented by the following formula (2) or formula (3):

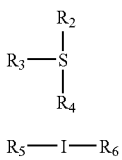

[Formula 2]

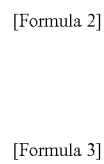

[Formula 3]

wherein $R_2$, $R_3$, $R_4$, $R_5$ and $R_6$ each independently represent a substituted or unsubstituted alkyl group having 1 to 20 carbon atoms, a substituted or unsubstituted allyl group having 3 to 10 carbon atoms, a substituted or unsubstituted perfluoroalkyl group having 1 to 10 carbon atoms, a substituted or unsubstituted benzyl group, or a substituted or unsubstituted aryl group having 6 to 30 carbon atoms; and two or more of $R_2$, $R_3$ and $R_4$ may be linked to each other to form a saturated or unsaturated carbon ring or a saturated or unsaturated heterocyclic ring.

According to another embodiment of the present invention, there is provided a polymer compound comprising a repeating unit represented by the following formula (5), a repeating unit represented by the following formula (6), and a repeating unit represented by the following formula (7):

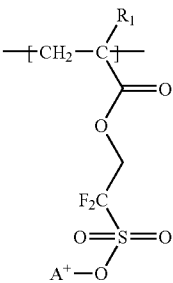

[Formula 5]

wherein $R_1$ represents a hydrogen atom, a trifluoromethyl group, an alkyl group having 1 to 5 carbon atoms, or an alkoxy group having 1 to 5 carbon atoms; and A represents a group represented by the following formula (2) or formula (3):

[Formula 2]

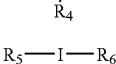

[Formula 3]

wherein $R_2$, $R_3$, $R_4$, $R_5$ and $R_6$ each independently represent a substituted or unsubstituted alkyl group having 1 to 20 carbon atoms, a substituted or unsubstituted allyl group having 3 to 10 carbon atoms, a substituted or unsubstituted perfluoroalkyl group having 1 to 10 carbon atoms, a substituted or unsubstituted benzyl group, or a substituted or unsubstituted aryl group having 6 to 30 carbon atoms; and two or more of $R_2$, $R_3$ and $R_4$ may be linked to each other to form a saturated or unsaturated carbon ring or a saturated or unsaturated heterocyclic ring;

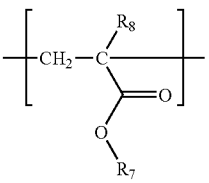

[Formula 6]

wherein $R_7$ represents a hydrogen atom, an alkyl group having 1 to 30 carbon atoms, or an alkyl group having 1 to 30 carbon atoms which is substituted with a group selected from an ether group, an ester group, a carbonyl group, an acetal group, an epoxy group, a nitrile group and an aldehyde group; and $R_8$ represents a hydrogen atom, a methyl group, or a trifluoromethyl group;

[Formula 7]

wherein X represents one selected from olefin, vinyl, styrene, and derivatives thereof.

The polymer compound according to an embodiment of the present invention preferably comprises three different species of the repeating unit represented by formula (6).

According to another embodiment of the present invention, there is provided a chemically amplified resist composition comprising the polymer compound according to the invention, an acid generator, additives, and a solvent.

According to another embodiment of the present invention, there is provided a method for forming a pattern, the method comprising: (a) applying the chemically amplified resist composition according to the invention on a substrate; (b) heat treating the substrate coated with the chemically amplified resist composition, and then exposing the substrate with high energy radiation; and (c) developing the outcome from the step (b) using a developer solution.

The compound represented by formula (1) according to the present invention is a novel compound, from which polymer compounds useful for chemically amplified resist compositions that are responsive to far-ultraviolet radiation, which is represented by KrF excimer laser or ArF excimer laser, can be produced. The chemically amplified resist composition is less dependent on the substrate, and has excellent adhesiveness, excellent transparency in the subject wavelength region, and excellent dry etch resistance, and a resist pattern excellent in sensitivity, resolution and developability can be formed from the resist composition.

DESCRIPTION OF THE PREFERRED EMBODIMENTS

Figure 1:
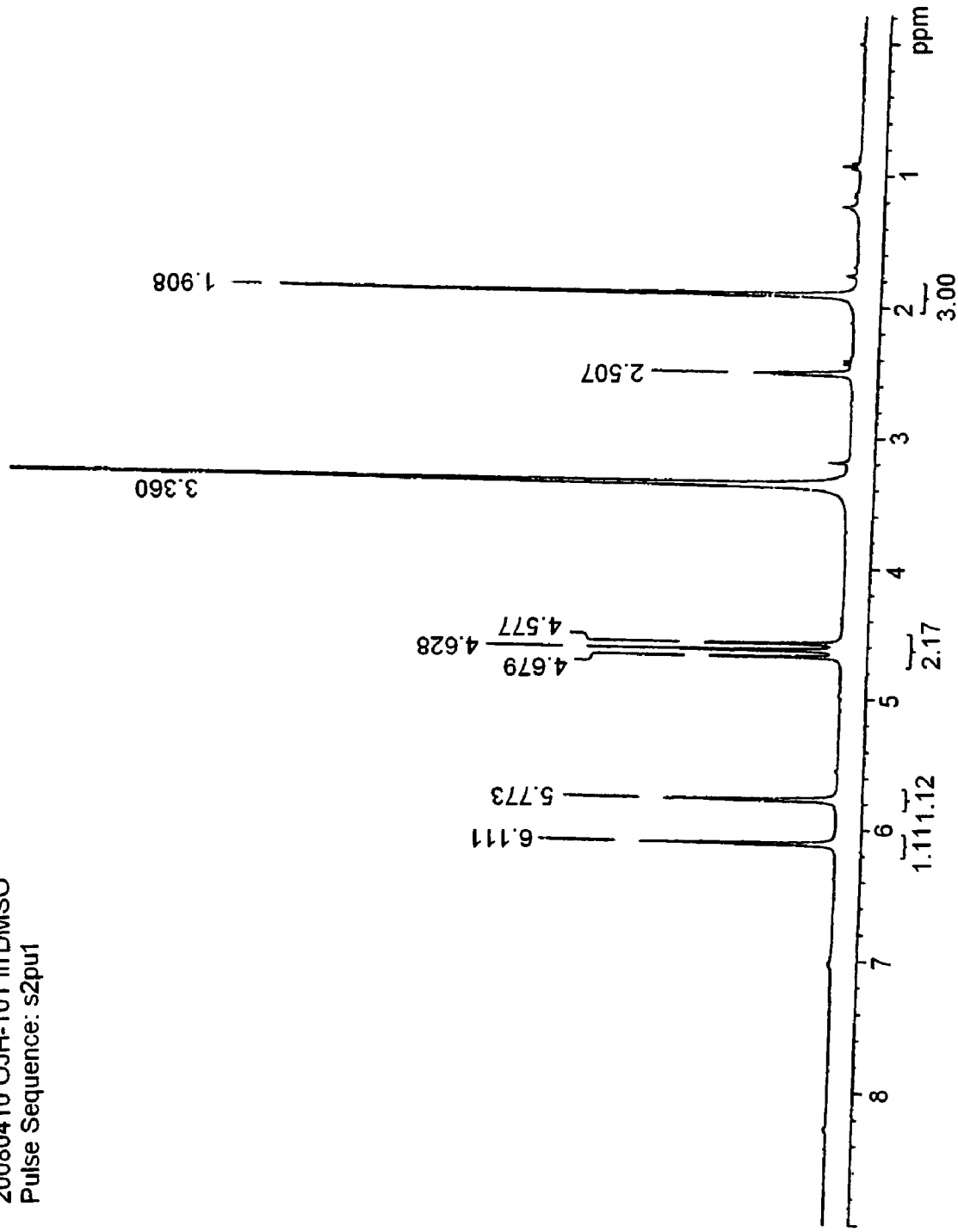
FIG. 1 shows the $^1$H-NMR spectrum of a compound according to an embodiment of the present invention.

Hereinafter, the present invention will be described in more detail.

According to an embodiment of the present invention, a compound represented by the following formula (1) is provided:

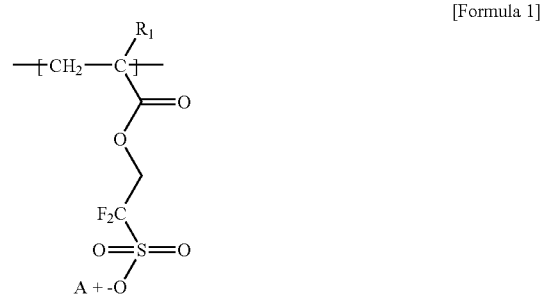

[Formula 1]

wherein $R_1$ represents a hydrogen atom, a trifluoromethyl group, an alkyl group having 1 to 5 carbon atoms, or an alkoxy group having 1 to 5 carbon atoms; and A represents a group represented by the following formula (2) or formula (3):

[Formula 2]

[Formula 3]

wherein $R_2$, $R_3$, $R_4$, $R_5$ and $R_6$ each independently represent a substituted or unsubstituted alkyl group having 1 to 20 carbon atoms, a substituted or unsubstituted allyl group having 3 to 10 carbon atoms, a substituted or unsubstituted perfluoroalkyl group having 1 to 10 carbon atoms, a substituted or unsubstituted benzyl group, or a substituted or unsubstituted aryl group having 6 to 30 carbon atoms; and two or more of $R_2$, $R_3$ and $R_4$ may be linked to each other to form a saturated or unsaturated carbon ring or a saturated or unsaturated heterocyclic ring.

In the formulas given in the present specification, the term "substituted" means that at least one hydrogen atom may be substituted with a halogen atom, a hydroxyl group, a nitro group, a cyano group, an amino group, an amidino group, a hydrazine group, a hydrazone group, a carboxyl group or a salt thereof, a sulfonic acid group or a salt thereof, a phosphoric acid group or a salt thereof, a $C_1$-$C_{10}$ alkyl group, a $C_1$-$C_{10}$ alkenyl group, a $C_1$-$C_{10}$ alkynyl group, a $C_6$-$C_{20}$ aryl group, a $C_7$-$C_{20}$ arylalkyl group, a $C_4$-$C_{20}$ heteroaryl group, or a $C_5$-$C_{20}$ heteroarylalkyl group.

The compound represented by formula (1) according to the present invention is a novel compound characterized by having a $SO_3^-(A^+)$ group at an end of the molecule. This compound of formula (1) can be used in the synthesis of a polymer compound which can be used in the chemically amplified resist composition that will be described later.
The moiety A in the formula (1) may be any one of the following formulas given as formula (4):
[Formula 4]
[Formula 4-a]
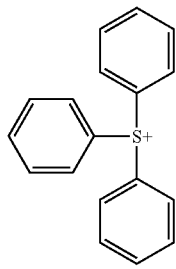
[Formula 4-b]
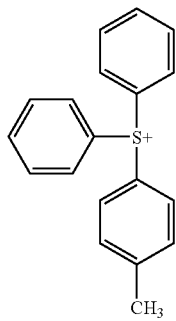
[Formula 4-c]
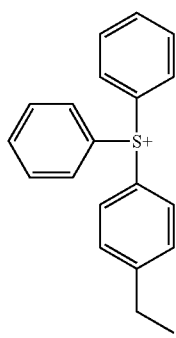
[Formula 4-d]
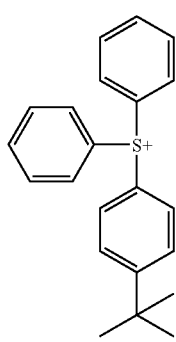
[Formula 4-e]
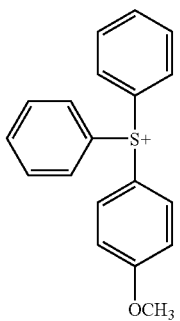
[Formula 4-f]
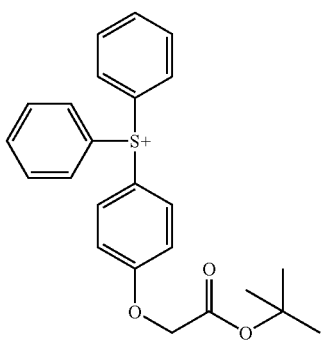
[Formula 4-g]
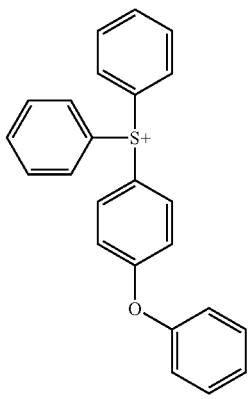
[Formula 4-h]
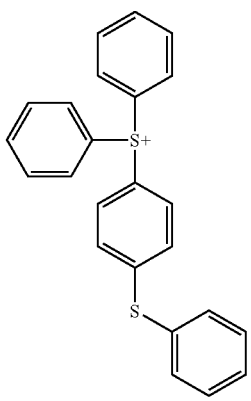

[Formula 4-i]
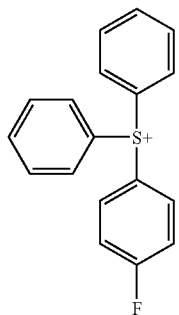
[Formula 4-j]
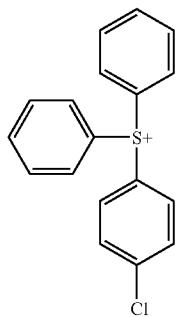
[Formula 4-k]
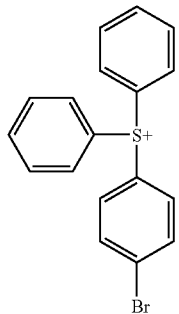
[Formula 4-l]
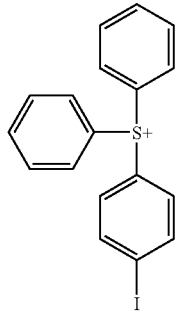
[Formula 4-m]
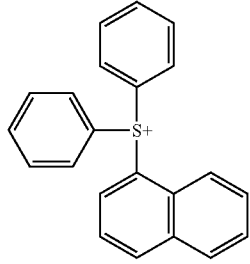
[Formula 4-n]
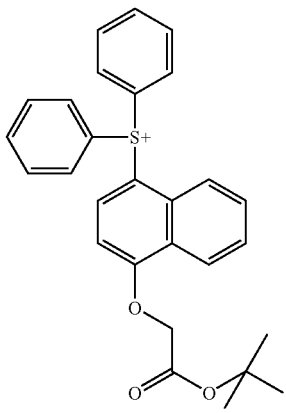
[Formula 4-o]
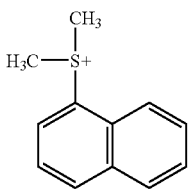
[Formula 4-p]
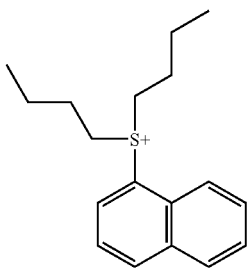
[Formula 4-q]
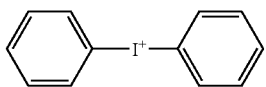
[Formula 4-r]
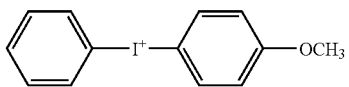
[Formula 4-s]
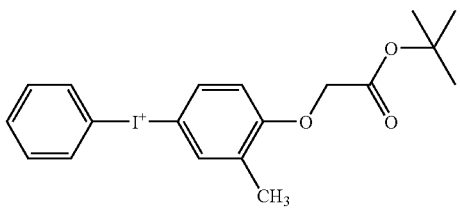
[Formula 4-t]
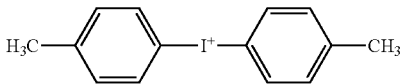
[Formula 4-u]

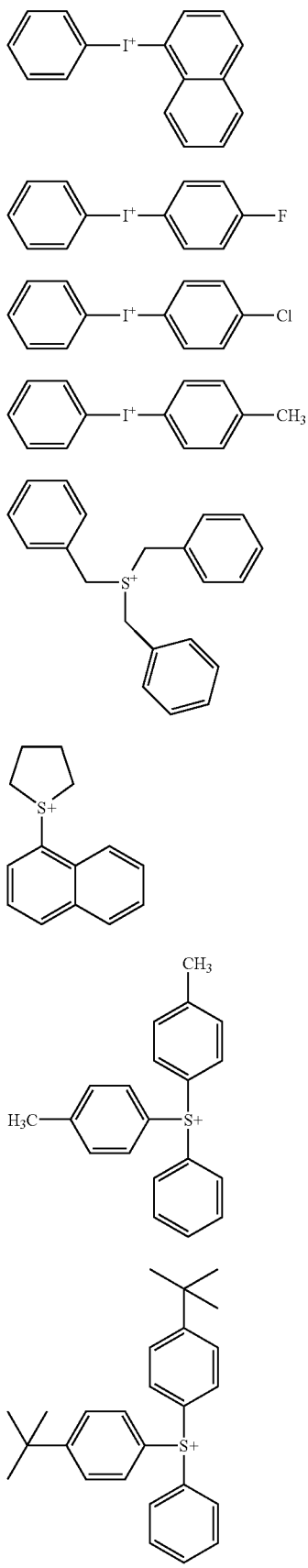

According to another embodiment of the present invention, there is provided a polymer compound comprising a repeating unit represented by the following formula (5), a repeating unit represented by the following formula (6), and a repeating unit represented by the following formula (7).

In the polymer compound according to the current embodiment of the invention, the repeating unit of formula (5), the repeating unit of formula (6) and the repeating unit of formula (7) may be randomly bound to form a block copolymer, a random copolymer, a graft copolymer or the like.

wherein $R_1$ represents a hydrogen atom, a trifluoromethyl group, an alkyl group having 1 to 5 carbon atoms, or an alkoxy group having 1 to 5 carbon atoms; and A represents a group represented by the following formula (2) or formula (3):

wherein $R_2$, $R_3$, $R_4$, $R_5$ and $R_6$ each independently represent a substituted or unsubstituted alkyl group having 1 to 20 carbon atoms, a substituted or unsubstituted allyl group having 3 to 10 carbon atoms, a substituted or unsubstituted perfluoroalkyl group having 1 to 10 carbon atoms, a substituted or unsubstituted benzyl group, or a substituted or unsubstituted aryl group having 6 to 30 carbon atoms; and two or more of $R_2$, $R_3$ and $R_4$ may be linked to each other to form a saturated or unsaturated carbon ring or a saturated or unsaturated heterocyclic ring;

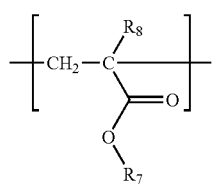

[Formula 6]

wherein $R_7$ represents a hydrogen atom, an alkyl group having 1 to 30 carbon atoms, or an alkyl group having 1 to 30 carbon atoms which is substituted with a group selected from an ether group, an ester group, a carbonyl group, an acetal group, an epoxy group, a nitrile group and an aldehyde group; and $R_8$ represents a hydrogen atom, a methyl group, or a trifluoromethyl group;

[Formula 7]

wherein X represents one selected from olefin, vinyl, styrene, and derivatives thereof.

According to a preferred embodiment, the polymer compound according to an embodiment of the present invention comprises 100 parts by weight of the repeating unit of formula (5), 100 to 700 parts by weight of the repeating unit of formula (6), and 100 to 300 parts by weight of the repeating unit of formula (7).

The polymer compound according to the embodiments of the present invention is useful as an ingredient for chemically amplified resist compositions. The reason why properties such as resolution, sensitivity, refractive index and line edge roughness are unsatisfactory in the existing resist compositions, may be that the polymer matrix and the photoacid generator (PAG) are not appropriately compatible to each other, and are not uniformly miscible. Therefore, in the present invention, it was attempted to directly attach the PAG to the polymer backbone and carry out polymerization, in order to solve the problem. More specifically, in the present invention, it was attempted to produce a polymer compound which allows introduction of a large quantity of a photoacid generator, and has faster sensitivity, higher stability, a reduced amount of gas generation, and low line edge roughness, by attaching the photoacid generator in an anion form to the polymer backbone, and to produce a resist composition comprising the polymer compound.

The polymer compound according to the embodiments of the present invention is a polymer compound in which a component having an acid-sensitive functional group and an acid generating component are incorporated together in one polymer molecule, which is, in other words, in the form of attaching a photoacid generator to the polymer.

The polymer compound according to the present invention has a polystyrene-reduced weight average molecular weight (hereinafter, referred to as "Mw") measured by gel permeation chromatography (GPC) of about 1,000 to about 100,000, and the weight average molecular weight is preferably about 1,000 to about 10,000, from the viewpoints of reduction as a photoresist, developability, coatability, thermal resistance and the like.

The molecular weight distribution of the polymer is preferably 1.0 to 5.0, and more preferably 1.0 to 3.0.

Among the most important characteristics for the semiconductor device processing which increasingly requires finer line widths, there may be mentioned line edge roughness.

According to the present invention, in order to solve the problem of miscibility between the photoacid generator, additives and polymers in the existing resist compositions, a polymer is produced by attaching a $SO_3^-(A^+)$ group which is capable of acting as a photoacid generator, to an end of an acryl monomer, and radical polymerizing the acryl monomer. Since such a polymer compound according to the present invention has a certain amount of photoacid generator attached to the polymer chain, the miscibility problem in the resist solvent can be solved even without adding any photoacid generator separately at the time of preparing a resist, and a pattern having high line edge roughness and high resolution can be realized. Furthermore, the polymer compound according to the present invention shows excellent transparency to the radiation during exposure, including immersion exposure, and has excellent basic properties required from a resist, such as sensitivity, resolution and pattern formability. In particular, the polymer compound can be used in a chemically amplified resist composition having high resolution, a broad depth of focus (DOF), and excellent line edge roughness.

According to a preferred embodiment, the moiety A is selected from the following formulas of formula (4):

[Formula 4]

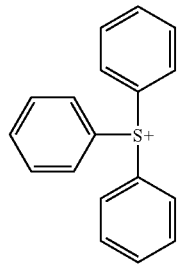

[Formula 4-a]

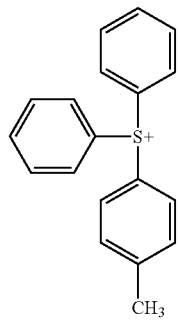

[Formula 4-b]

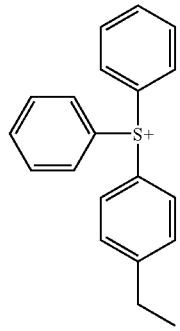

[Formula 4-c]

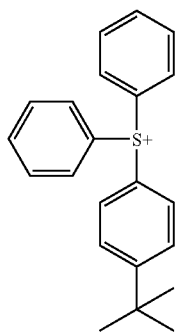
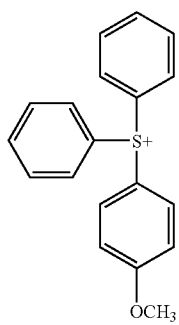
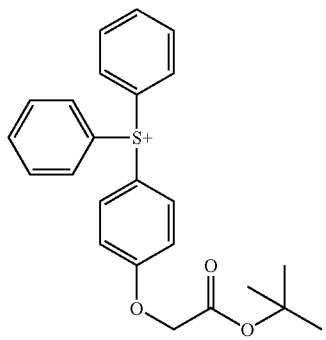
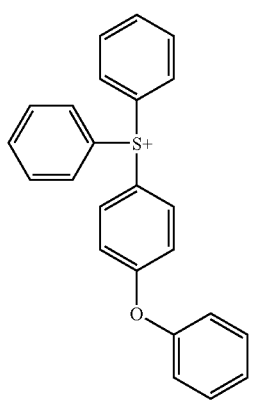
[Formula 4-d]
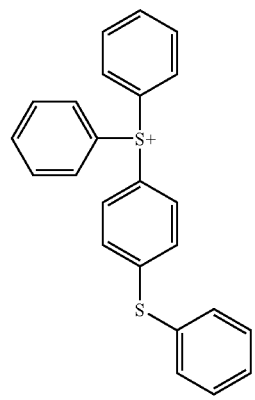
[Formula 4-e]
[Formula 4-f]
[Formula 4-g]
[Formula 4-h]
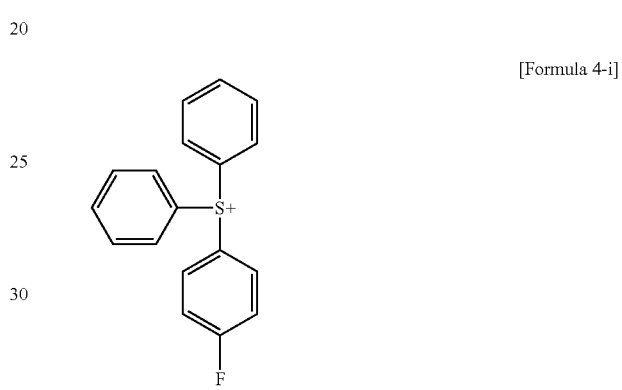
[Formula 4-i]
[Formula 4-j]
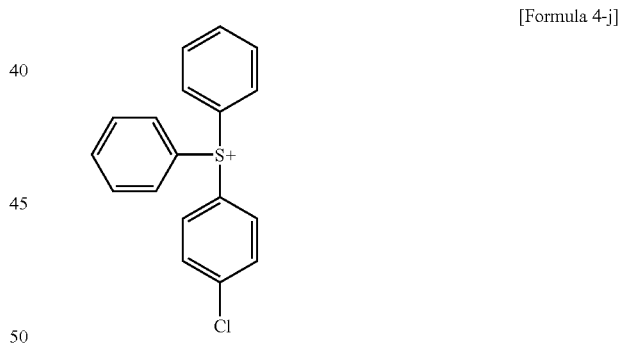
[Formula 4-k]
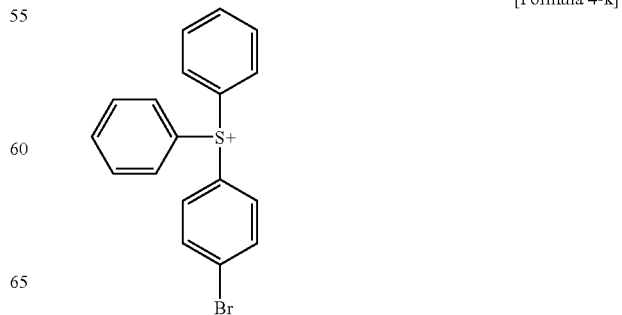

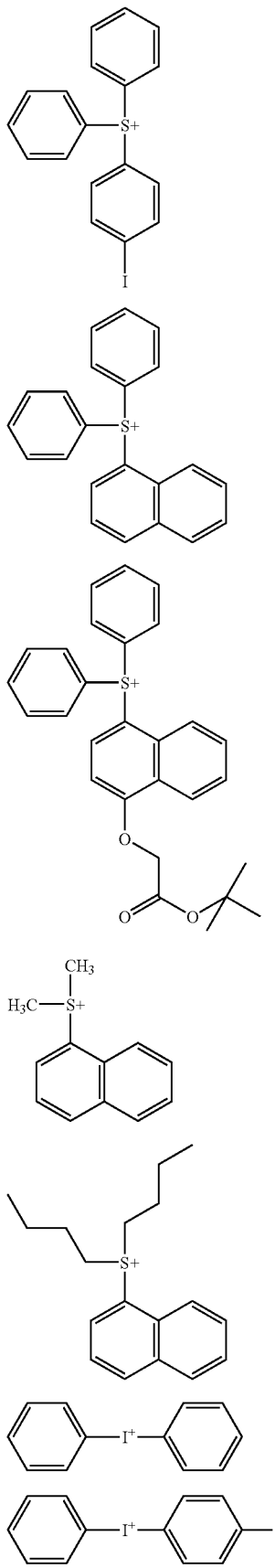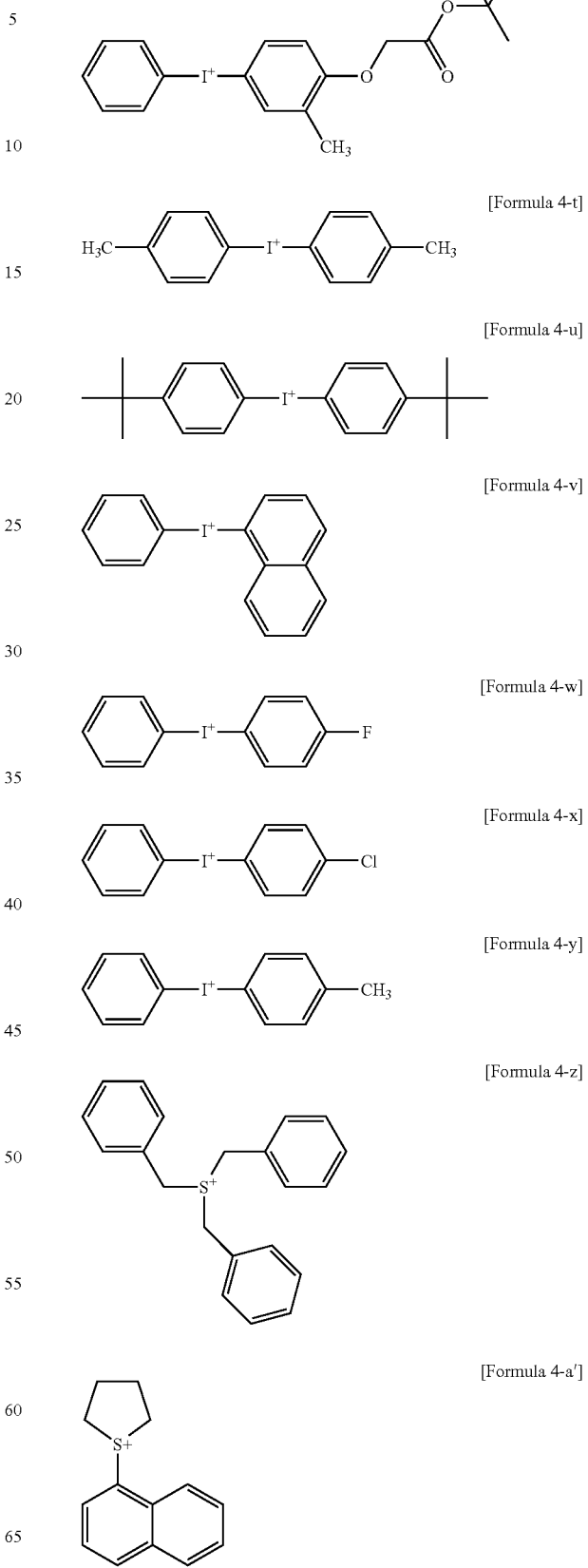

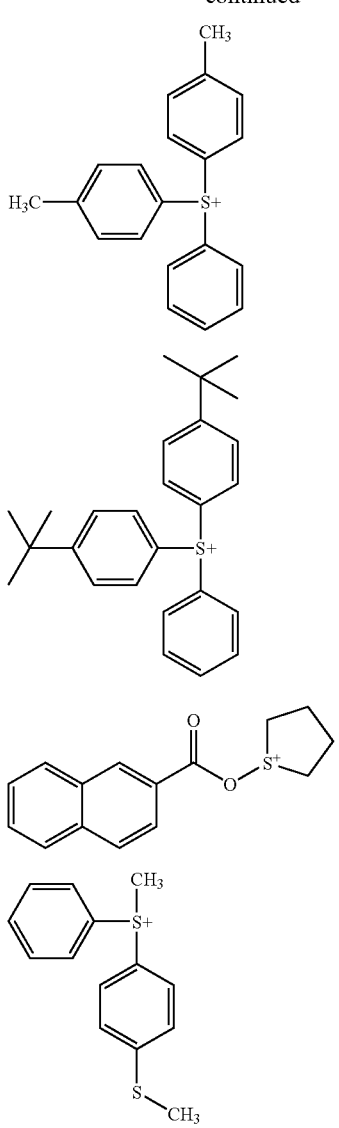

The polymer compound according to an embodiment of the present invention has a methacrylate monomer containing a sulfonium salt, an acrylate monomer, and an olefin monomer, as the repeating units. Optionally, the polymer may be synthesized in the presence of vinyl ether. The polymer compound according to embodiments of the present invention is generally insoluble or sparing soluble per se in aqueous alkali solutions, but in some cases, the polymer may also be soluble in aqueous alkali solutions. Furthermore, the polymer comprises the compound of formula (5) having an acid-labile functional group in the side chain part, but may optionally comprise a compound of formula (6) or a compound of formula (7), which are repeating units not having the aforementioned functional group. The solubility may increase or decrease, depending on the type and content of the monomers in the polymer. In general, as there are more hydrophobic groups, the solubility in aqueous alkali solutions is decreased.

According to another preferred embodiment, the polymer compound comprising the repeating unit of formula (5), the repeating unit of formula (6) and the repeating unit of formula (7) according to the present invention, comprises three different species of the repeating unit of formula (6). Such a polymer compound is represented in the present specification by the following formula (8):

[Formula 8]

wherein $R_1$ represents a hydrogen atom, a trifluoromethyl group, an alkyl group having 1 to 5 carbon atoms, or an alkoxy group having 1 to 5 carbon atoms; $R_{7a}$, $R_{7b}$ and $R_{7c}$ each independently represent a hydrogen atom, a linear or branched alkyl group having 1 to 30 carbon atoms, or a linear or branched alkyl group having 1 to 30 carbon atoms which is substituted with an ether group, an ester group, a carbonyl group, an acetal group, an epoxy group, a nitrile group or an aldehyde group; $R_{8a}$, $R_{8b}$ and $R_{8c}$ each independently represent a hydrogen atom, a methyl group or a trifluoromethyl group; and A has the same meaning as defined previously.

More specifically, the polymer compound represented by the formula (8) according to the present invention may be represented by any one of the following compounds of formula (9):

[Formula 9]

[Formula 9-a]

[Formula 9-b]
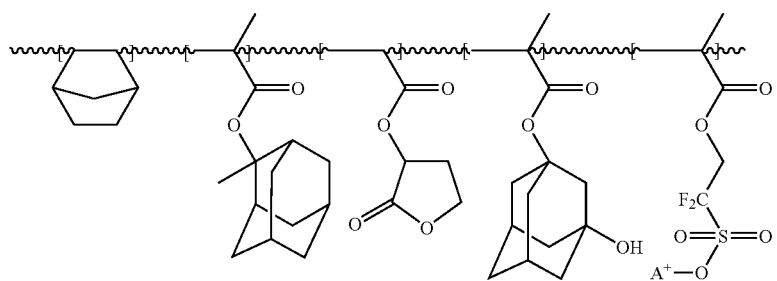
[Formula 9-c]
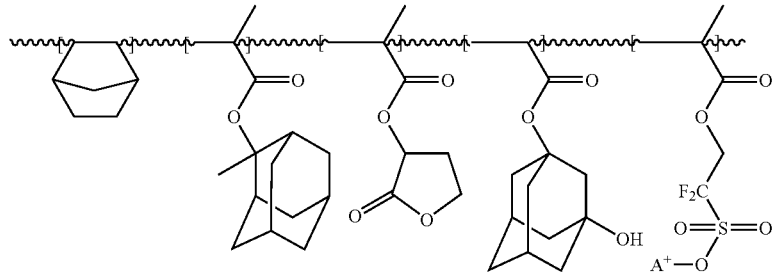
[Formula 9-d]
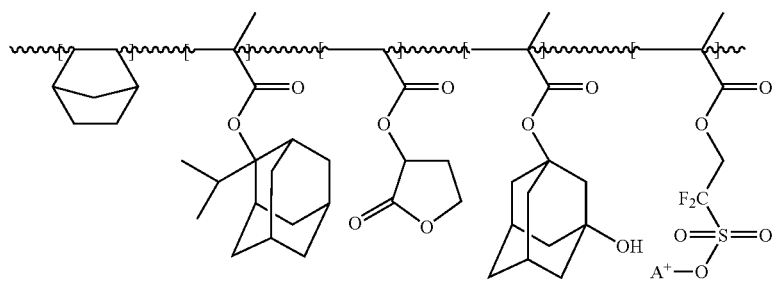
[Formula 9-e]
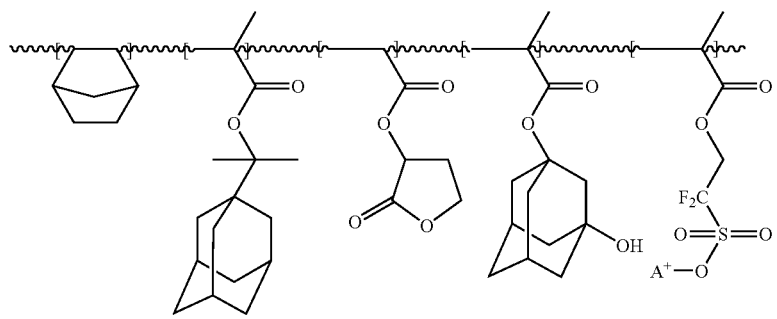
[Formula 9-f]
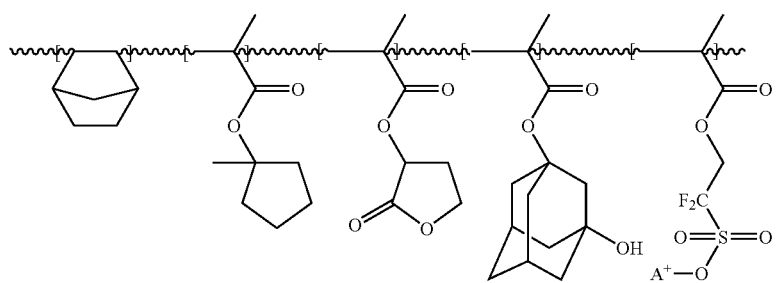

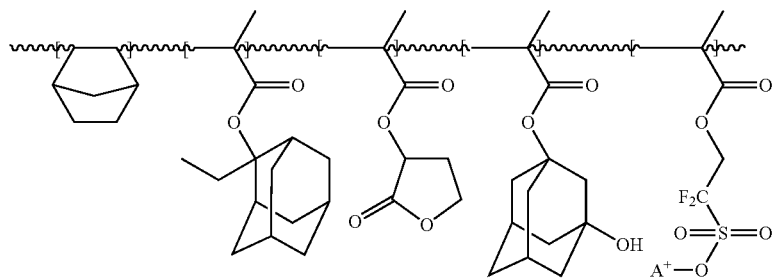
[Formula 9-g]
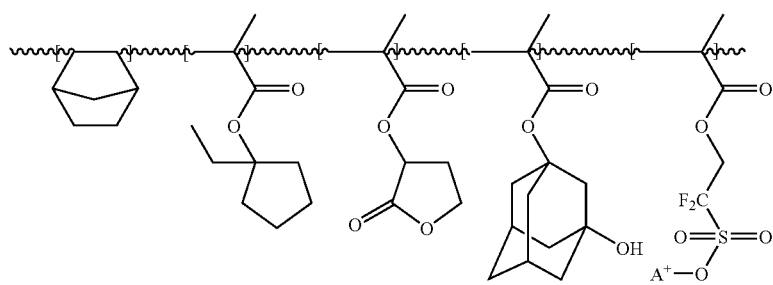
[Formula 9-h]
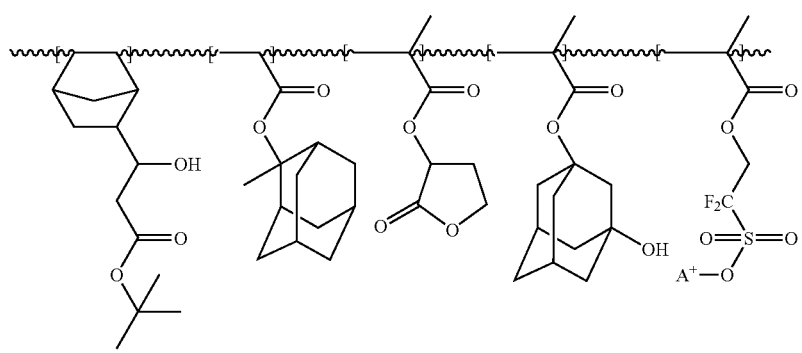
[Formula 9-i]
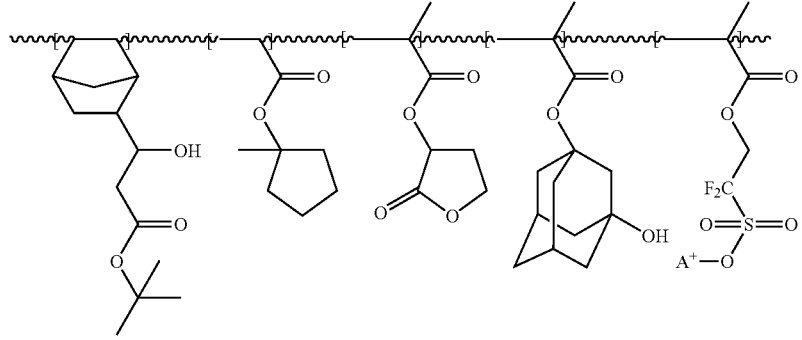
[Formula 9-j]
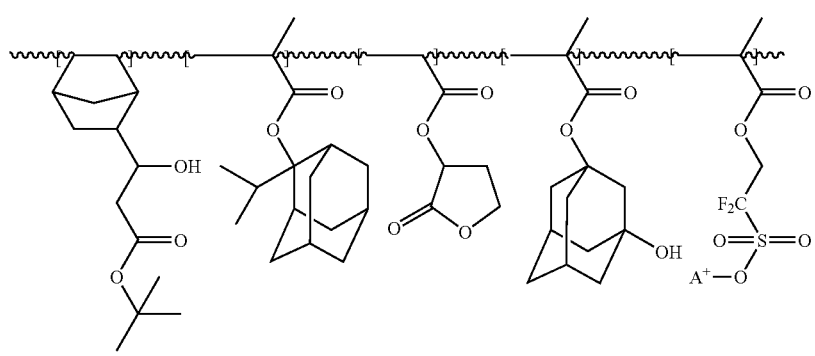
[Formula 9-k]

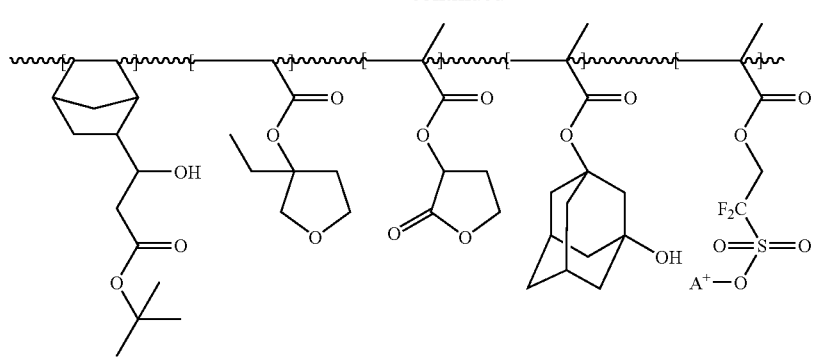

[Formula 9-1]

Hereinafter, the method for producing the compound represented by formula (1) according to the present invention will be described.

The compound of formula (1) is produced by a reaction between compounds of the following formula (10) and formula (11):

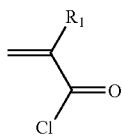

[Formula 10]

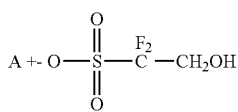

[Formula 11]

wherein $R_1$ and A have the same meanings as defined for the formula (1).

Specifically, in the method of such reaction, generally an alcohol of formula (11) and acryloyl chloride of formula (10) are dissolved in a reaction solvent such as dichloromethane, chloroform, dichloroethane, acetonitrile, toluene, benzene or 1,4-dioxane at a temperature of 0 to 100° C., and then the solution can be made to react using a basic catalyst such as triethylamine, diethylamine, pyridine, diethylisopropylamine, aniline or diisopropylethylamine in an amount of 1 mole to 2 moles based on the reactant, the alcohol of formula (11).

In regard to the method for producing the alcohol of formula (11), an ester compound such as one represented by the following formula (12) is dissolved using tetrahydrofuran and an alcoholic solvent such as methanol, ethanol or propanol, and in an ice bath, sodium borohydride (NaBH$_4$) is slowly added dropwise. When the dropwise addition is completed, the mixture is stirred in an oil bath at 60° C. for about 4 hours, and then the reaction mixture liquid is quenched with distilled water to remove the solvent. The reaction mixture liquid from which the solvent has been removed is dissolved again in distilled water, and then the solution is acidified using concentrated hydrochloric acid until a pH value of 5 to 6 is obtained. The mixture liquid is concentrated again, subsequently methanol is added to make the mixture liquid into a slurry, and the slurry is filtered. The filtrate is washed using hexane, and then concentrated again. The concentrate is subjected to crystallization using diethyl ether, and then filtered and dried, and thus an alcohol such as the one of formula (11) can be produced.

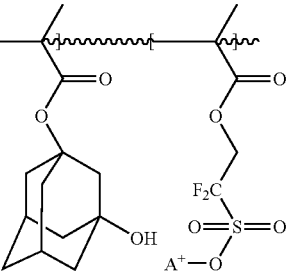

[Formula 12]

wherein $R_1'$ is selected from the group consisting of hydrogen, methyl, trifluoromethyl, trichloromethyl, tribromomethyl and triiodomethyl; and M represents lithium (Li), sodium (Na) or potassium (K).

Hereinafter, the method for producing the polymer compound comprising the repeating unit of formula (5), the repeating unit of formula (6) and the repeating unit of formula (7) according to the present invention will be described.

The method of polymerizing the polymer compound according to the present invention may be achieved by a conventional method, but according to an embodiment, radical polymerization is preferred. The radical polymerization initiator is not particularly limited as long as it is an initiator used as a general radical polymerization initiator, such as azobisisobutyronitrile (AIBN), benzoyl peroxide (BPO), lauryl peroxide, azobisisocapronitrile, azobisisovaleronitrile or tert-butyl hydroperoxide. The polymerization reaction can be carried out by methods such as bulk polymerization, solution polymerization, suspension polymerization, bulk-suspension polymerization and emulsion polymerization, and as for the polymerization solvent, one or more can be selected from benzene, toluene, xylene, halogenated benzene, diethyl ether, tetrahydrofuran, 1,2-dichloroethane, esters, ethers, lactones, ketones and amides, and used. The polymerization temperature for the polymer compound according to the present invention is appropriately selected and used according to the type of the catalyst. The molecular weight distribution of the polymer can be appropriately controlled by changing the amount of use of the polymerization initiator and the reaction time. After the polymerization comes to completion, it is preferable to remove any unreacted monomers and side products remaining in the reaction mixture by a precipitation method using a solvent.

The polymer compound according to the present invention may further comprise a repeating unit having an acid-labile group, and a repeating unit containing a hydroxyl group, a lactone ring group, or both a hydroxyl group and a lactone ring group.

According to another embodiment of the present invention, there is provided a chemically amplified resist composition comprising the polymer compound according to the present invention, additives and a solvent. The chemically amplified resist composition according to the present invention may further comprise an acid generator such as triphenylsulfonium nonaflate.

In order to improve the properties of the chemically amplified resist composition, conventionally used additives may be used. Specific examples thereof include dissolution inhibitor, basic additives, defoaming agent, surfactant, acid diffusion controlling agent, adhesion aid, and the like. As the dissolution inhibitor, norbornane-based cyclic-structured substances can be used, and such low molecular weight compound additives can not only enhance the dry etch resistance by introducing a cyclic structure into the molecule, but also can enhance film remaining characteristics at non-exposed parts. At the exposed parts, the additives can accelerate dissolution in alkali developer solutions under the action of acid, and further enhance the contrast at the time of development, to thereby more effectively improve the perpendicularity of resist pattern side walls. Examples of the compound which is degraded by acid and accelerates the rate of dissolution in a developer solution, include alicyclic derivatives having a functional group which can be easily changed to a deprotecting group by acid. The low molecular weight compound additives provided by the present invention are norbornane-based compounds represented by the formula (2) or (3), in which the double bond in the norbornene-based monomer has been reduced by a hydrogenation reaction. Examples of the norbornane-based low molecular weight compounds include compounds having the following structures. These low molecular weight compounds can be used individually alone, or as mixtures of two or more species. The amount of use of the low molecular weight compound at the time of resist production is 3 to 50 parts by weight, and preferably 5 to 40 parts by weight, based on 100 parts by weight of the polymer. If the amount of addition of the low molecular weight compound is less than 3 parts by weight, the effects expected from the additive are not manifested, while if the amount of addition is greater than 50 parts by weight, the adhesiveness to the substrate and coatability tend to greatly decrease.

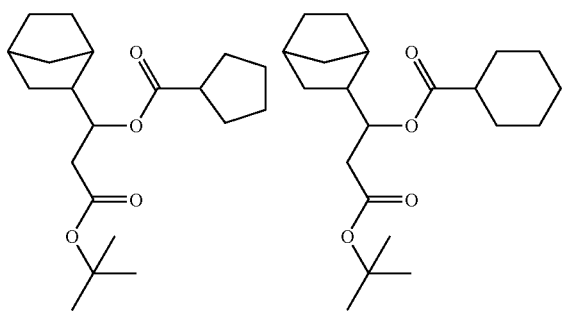

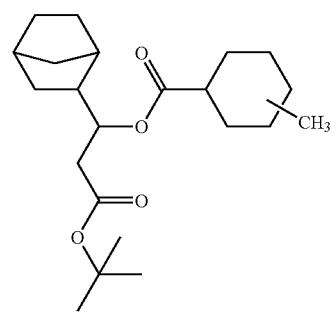

-continued

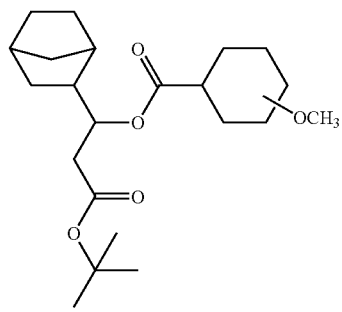

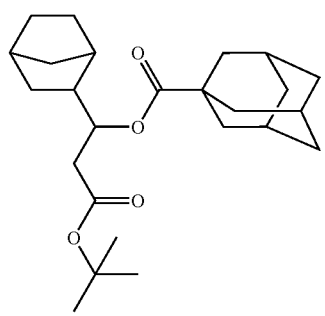

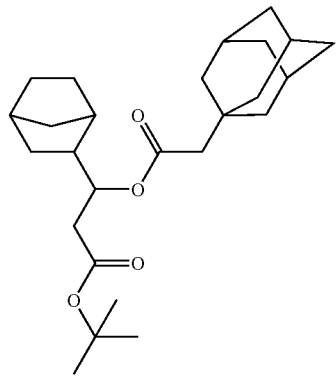

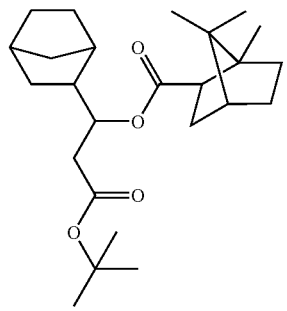

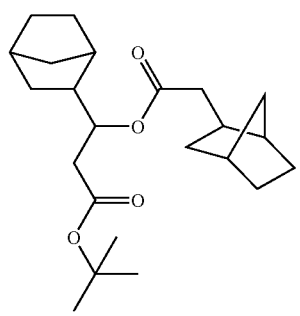

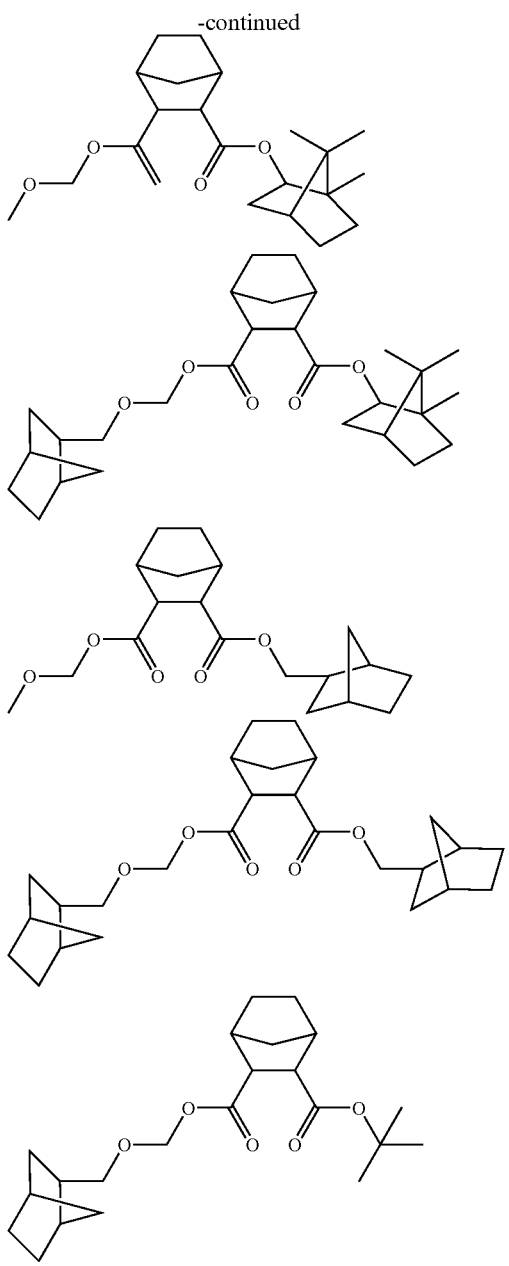

According to a preferred embodiment, the total content of the additives is 0.1 to 10 parts by weight based on 100 parts by weight of the polymer compound according to the present invention.

In regard to the solvent, those conventionally contained in chemically amplified resist compositions can be used, and specific examples of the solvent include propylene glycol monomethyl ether acetate, ethyl lactate, cyclohexanone, butyl lactate, propylene glycol monomethyl ether, and the like.

According to another preferred embodiment, the content of the moiety —$(SO_3)^-(A)^+$ in the polymer compound is 0.5 parts by weight to 15 parts by weight based on 100 parts by weight of the total solid content of the chemically amplified resist composition. If the content of the moiety —$(SO_3)^-(A)^+$ is less than 0.5 parts by weight based on 100 parts by weight of the total solid content of the chemically amplified resist composition, there may be a problem that the amount of acid generated after exposure is so small that the protective group of the polymer is not detached, and a pattern of desired form cannot be obtained. If the content exceeds 15 parts by weight, excessive generation of acid may cause losses in the upper parts of the profile, and thus may cause a problem in the ratio of remaining film.

According to another preferred embodiment, the content of the polymer compound according to the present invention in the chemically amplified resist composition of the invention is 3% by weight or more, preferably 5% by weight or more, and more preferably 5% by weight to 10% by weight, based on the chemically amplified resist composition. If the content of the polymer compound according to the present invention is less than 3% by weight of the chemically amplified resist composition, there may be a problem that a film having a desired thickness cannot be obtained.

According to another embodiment of the present invention, there is provided a method for forming a pattern, the method comprising:

(a) applying the chemically amplified resist composition according to the present invention on a substrate;

(b) heat treating the substrate coated with the chemically amplified resist composition, and then exposing the substrate with high energy radiation; and (c) developing the outcome from the step (b) using a developer solution.

The exposure of the step (b) can be carried out using ultraviolet irradiation, X-ray irradiation, or an electron beam irradiation.

According to a preferred embodiment, the wavelength of the high energy radiation is in the range of 180 nm to 250 nm.

The developer solution used in the development of the step (c) can be selected from aqueous solutions containing sodium hydroxide, potassium hydroxide, sodium carbonate, sodium silicate, sodium metasilicate, ammonia water, ethylamine, n-propylamine, triethylamine, tetramethylammonium hydroxide, tetraethylammonium hydroxide or the like. Particularly, among them, tetramethylammonium hydroxide is preferred. If necessary, additives such as surfactants and water-soluble alcohols may also be used.

The present invention will be specifically described by way of the following Synthesis Examples and Examples. However, the present invention is not intended to be limited to these Synthesis Examples and Examples.

Synthesis Example 1

In an ice bath, 83 g of difluorosulfoacetic acid ethyl ester sodium salt was dissolved in 160 ml of methanol and 1.2 L of THF, and 44 g of sodium borohydride (NaBH$_4$) was slowly added dropwise. After completing the dropwise addition, the ice bath was removed, and the temperature was elevated to 60° C., at which temperature the mixture was stirred for about 4 hours.

After the reaction, the reaction mixture liquid was quenched with distilled water, and then the solvent was removed. The crude reaction mixture was dissolved again in distilled water, and the solution was acidified with concentrated hydrochloric acid to obtain a pH value of 5. The system was concentrated, and then methanol was added to form a slurry. This slurry was filtered to remove inorganic salts, and the filtrate was washed two times with hexane. The methanol layer was concentrated again, and then was subjected to crystallization from diethyl ether. White solids were obtained by filtration, which were dried in a vacuum, and the structure of the solids was confirmed by $^1$H-NMR. After drying and filtration, 68.5 g (yield 95%) of difluorohydroxyethanesulfonic acid sodium salt was obtained.

$^1$H-NMR (chloroform-$d_3$, internal standard: tetramethylsilane): (ppm) 4.58-4.68 (t, 2H)

[Reaction Scheme 1]

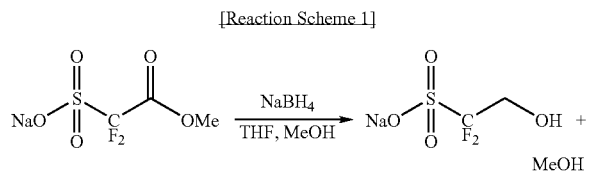

Synthesis Example 2

68 g of the difluorohydroxyethanesulfonic acid sodium salt produced in the Synthesis Example 1 and 54.6 ml of methacryloyl chloride were mixed with 500 ml of dichloromethane, and the mixture was stirred. Subsequently, 3.2 g of N,N'-dimethylaminopyridine and 50 mg of AIBN (2,2'-azobisisobutyronitrile; Wako Pure Chemical Industries, Ltd.) were added thereto at ambient temperature. 104 ml of triethylamine was slowly added dropwise using a dropping funnel at ambient temperature. The resulting mixture was stirred for 3 hours at ambient temperature, subsequently the progress of the reaction was judged by NMR, and the reaction was terminated. After completion of the reaction, the reaction solvent dichloromethane was removed by distillation under reduced pressure, 300 ml of water was added, and then potassium carbonate was added to the reaction liquid to obtain a saturated solution. The solution was stirred for 2 hours, and then generated solids were filtered, to thus obtain 81 g (yield: 86%) of 2-methylacrylic acid-2,2-difluoro-2-sulfoethyl ester sodium salt having a desired structure as shown in the following reaction scheme 2. The structure of the product was confirmed by $^1$H-NMR (see FIG. 1).

$^1$H-NMR (DMSO, internal standard: tetramethylsilane): (ppm) 1.91 (s, 3H), 4.57-4.67 (t, 2H), 5.77 (s, 1H), 6.11 (s, 1H)

[Reaction Scheme 2]

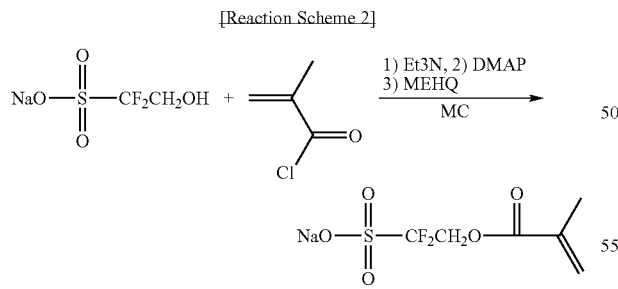

Synthesis Example 3

31 g of the 2-methylacrylic acid-2,2-difluoro-2-sulfoethyl ester sodium salt produced in the Synthesis Example 2 and 35 g of diphenylmethylphenylsulfonium-2-methyl acrylic acid 2,2-difluoro-2-sulfonic acid salt were dissolved in 300 ml of dichloromethane and 300 ml of water, and a two-layer reaction was performed while stirring vigorously for 3 hours.

Figure 2:
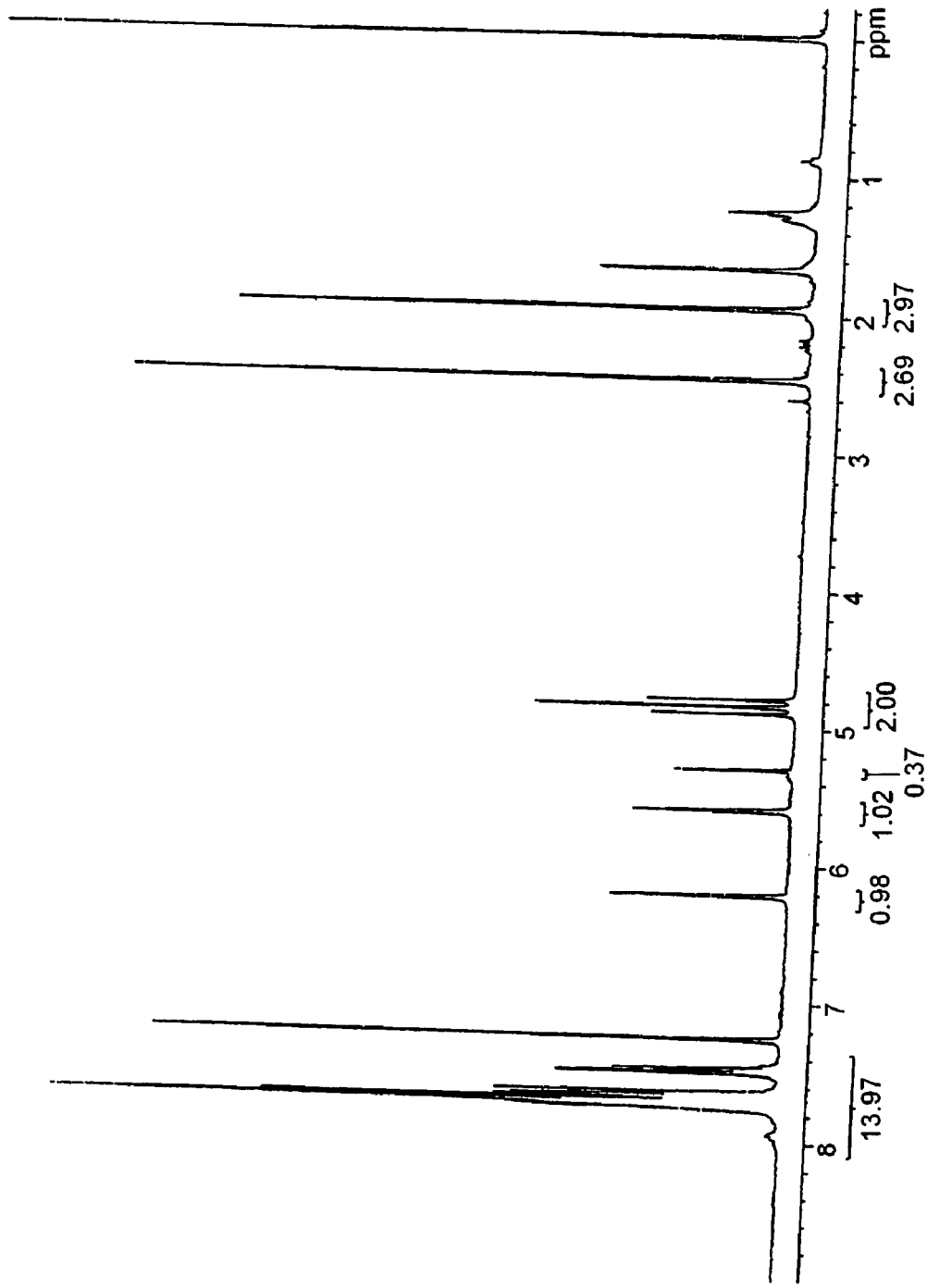
FIG. 2 shows the $^1$H-NMR spectrum of a compound according to another embodiment of the present invention.

After completing the stirring, the organic layer was removed, and the progress of the reaction was checked by $^{19}$F-NMR. When the reaction was completed, the organic layer was collected, and the solvent was removed. The organic layer was washed using dichloromethane, which is a good solvent, and hexane, which is a poor solvent, and the solvents were removed. The residues were dried under reduced pressure to obtain 40 g (yield: 96%) of 2-methylacrylic acid-2,2-difluoro-2-sulfoethyl ester diphenylfluorophenylsulfonium salt, and the structure of the product was confirmed by $^1$H-NMR (see FIG. 2).

$^1$H-NMR (chloroform-$d_3$, internal standard: tetramethylsilane): (ppm) 1.95 (s, 3H), 2.43 (s, 3H), 4.82 (t, 2H), 5.60 (s, 1H), 6.22 (s, 1H), 7.43-7.80 (m, 14H)

[Reaction Scheme 3]

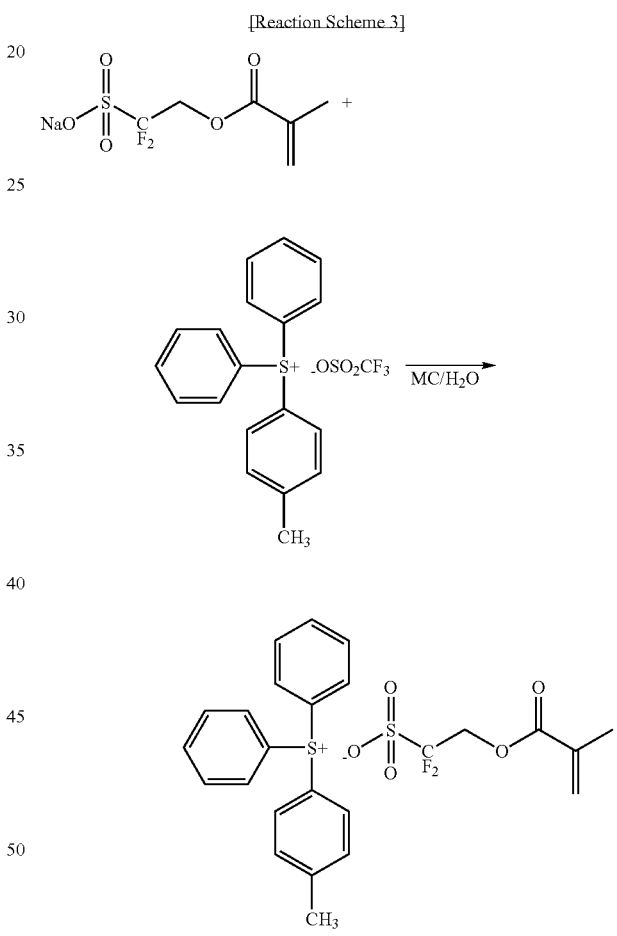

Synthesis Example 4

30 g of the difluorohydroxyethanesulfonic acid sodium salt produced in the Synthesis Example 1 and 20 ml of acryloyl chloride were mixed with 300 ml of dichloromethane, and the mixture was stirred. Subsequently, 1.4 g of N,N'-dimethylaminopyridine and 38 g of a polymerization inhibitor were added to the mixture at ambient temperature. 45 ml of triethylamine was slowly added dropwise using a dropping funnel at ambient temperature. The resulting mixture was stirred for 3 hours at ambient temperature, subsequently the progress of the reaction was judged by NMR, and the reaction was terminated. After completion of the reaction, the reaction solvent dichloromethane was removed by distillation under reduced pressure, 300 ml of water was added, and then potassium carbonate was added to the reaction liquid to obtain a saturated solution. The solution was stirred for 2 hours, and then generated solids were filtered, to thus obtain 35 g (yield: 90%) of 2-acrylic acid-2,2-difluoro-2-sulfoethyl ester sodium salt having a desired structure as shown in the following reaction scheme. The structure of the product was confirmed by $^1$H-NMR.

[Reaction Scheme 4]

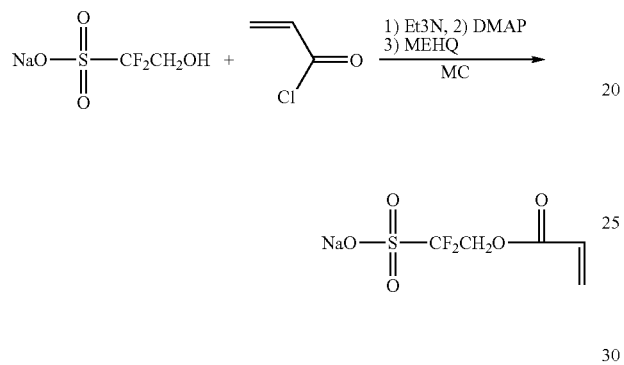

Synthesis Example 5

20 g of the 2-acrylic acid-2,2-difluoro-2-sulfoethyl ester sodium salt produced in the Synthesis Example 4 and 35 g of diphenylmethylphenylsulfonium trifluoromethanesulfonate salt were dissolved in 200 ml of dichloromethane and 200 ml of water, and a two-layer reaction was performed while stirring vigorously for 3 hours.

After completing the stirring, the organic layer was removed, and the progress of the reaction was checked by $^{19}$F-NMR. When the reaction was completed, the organic layer was collected, and the solvent was removed. The organic layer was washed using dichloromethane, which is a good solvent, and hexane, which is a poor solvent, and the solvents were removed. The residues were dried under reduced pressure to obtain 36 g (yield: 89%) of 2-acrylic acid-2,2-difluoro-2-sulfoethyl ester diphenylfluorophenylsulfonium salt, and the structure of the product was confirmed by $^1$H-NMR.

$^1$H-NMR (chloroform-d$_3$, internal standard: tetramethylsilane): (ppm) 1.95 (s, 3H), 2.43 (s, 3H), 4.82 (t, 2H), 5.78 (d, 1H), 6.00 (dd, 1H), 6.28 (d, 1H), 7.43-7.80 (m, 14H)

[Reaction Scheme 5]

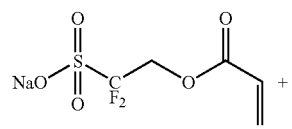

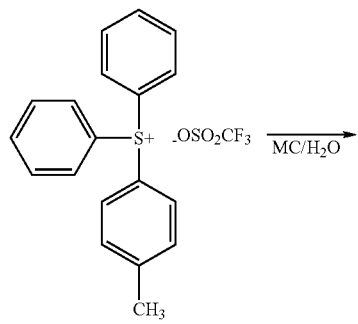

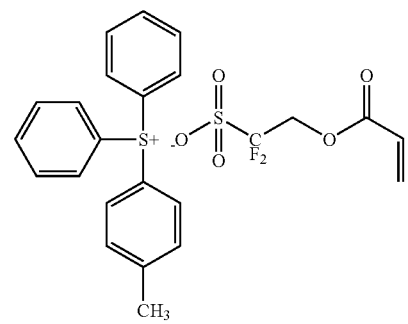

Synthesis Example 6

As the monomers for polymerization, 13 g of 2-methyl-2-adamantyl acrylate, 8.4 g of γ-butyrolactyl methacrylate, 11.6 g of 3-hydroxy-1-adamantyl methacrylate, and 10 g of 2-methylacrylic acid-2,2-difluoro-2-sulfoethyl ester diphenylfluorophenylsulfonium salt were first dissolved in 58 g of 1,2-dichloroethane. Next, 3.7 g of norbornene, 2.5 g of AIBN as a polymerization initiator, and 117 g of 1,2-dichloroethane as a polymerization solvent were placed in a 250-ml flask, and then the mixture was stirred for 1 hour at ambient temperature under a nitrogen gas stream. While maintaining the temperature of the reaction tank at 65° C., the dissolved monomers for polymerization were slowly added dropwise to the flask over 1 hour, and then the reaction was allowed to proceed for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 37 g (yield: 79%) of the polymer represented by formula (13).

Figure 3:
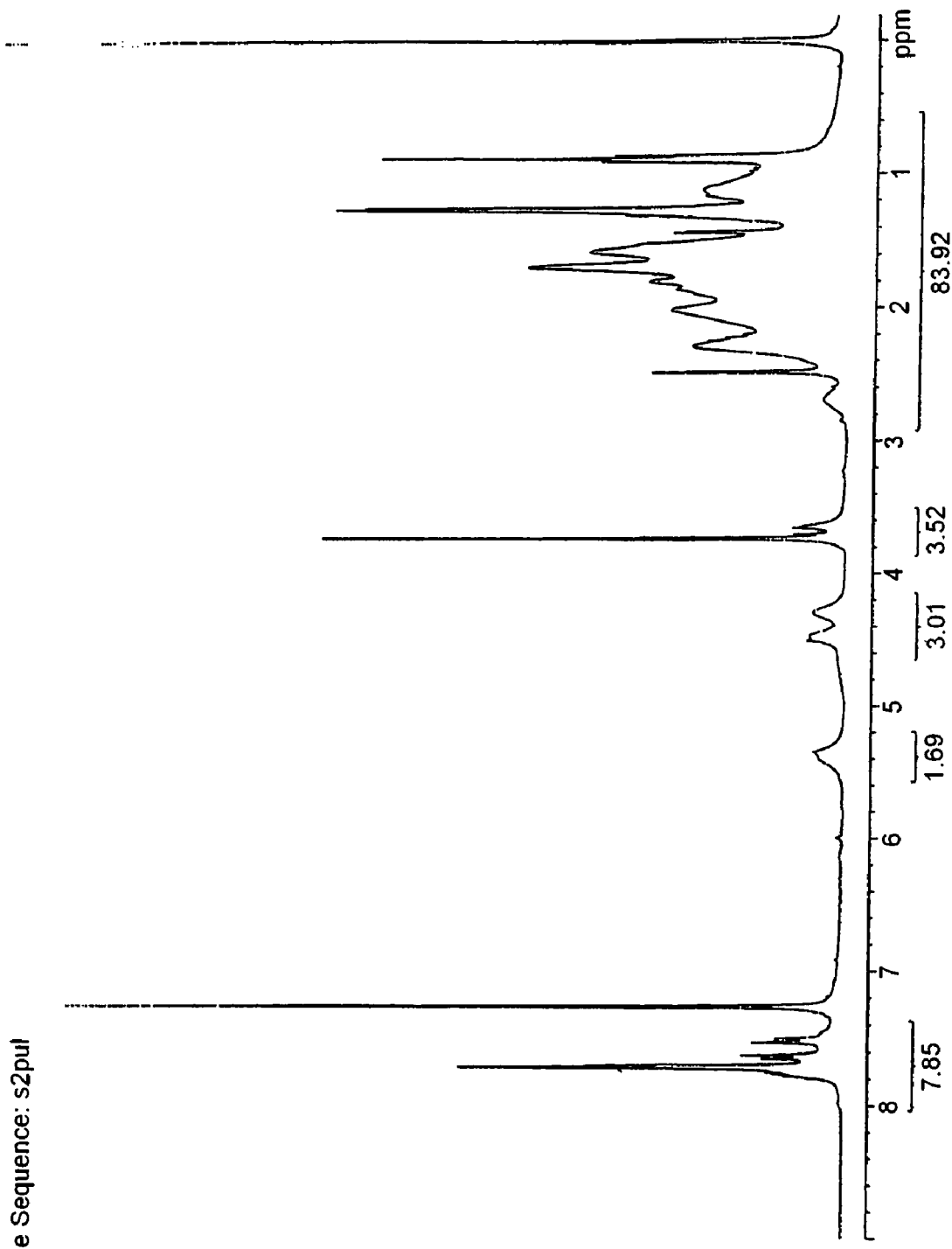
FIG. 3 shows the $^1$H-NMR spectrum of a compound according to still another embodiment of the present invention.

The polystyrene-reduced weight average molecular weight (Mw) of this polymer was 1,190, and the molecular weight distribution (ratio of the weight average molecular weight to the number average molecular weight, Mw/Mn) was 1.57. FIG. 3 shows the $^1$H-NMR spectrum of this polymer.

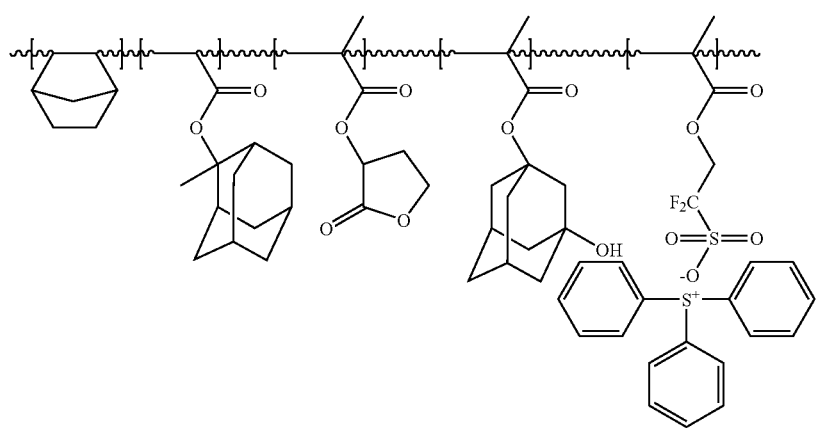

[Formula 13]

Synthesis Example 7

As the monomers for polymerization, 15.2 g of 2-methylpentyl acrylate, 10 g of γ-butyrolactyl methacrylate, 10 g of 3-hydroxy-1-adamantyl methacrylate, and 4 g of 2-methylacrylic acid-2,2-difluoro-2-sulfoethyl ester diphenylfluorophenylsulfonium salt were first dissolved in 49 g of 1,2-dichloroethane. Next, 3.7 g of norbornene, 5 g of AIBN as a polymerization initiator, and 98 g of 1,2-dichloroethane as a polymerization solvent were placed in a 250-ml flask, and then the mixture was stirred for 1 hour at ambient temperature under a nitrogen gas stream. While maintaining the temperature of the reaction tank at 65° C., the dissolved monomers for polymerization were slowly added dropwise to the flask over 1 hour, and then the reaction was allowed to proceed for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 31 g (yield: 81%) of the polymer represented by formula (14).

Figure 4:
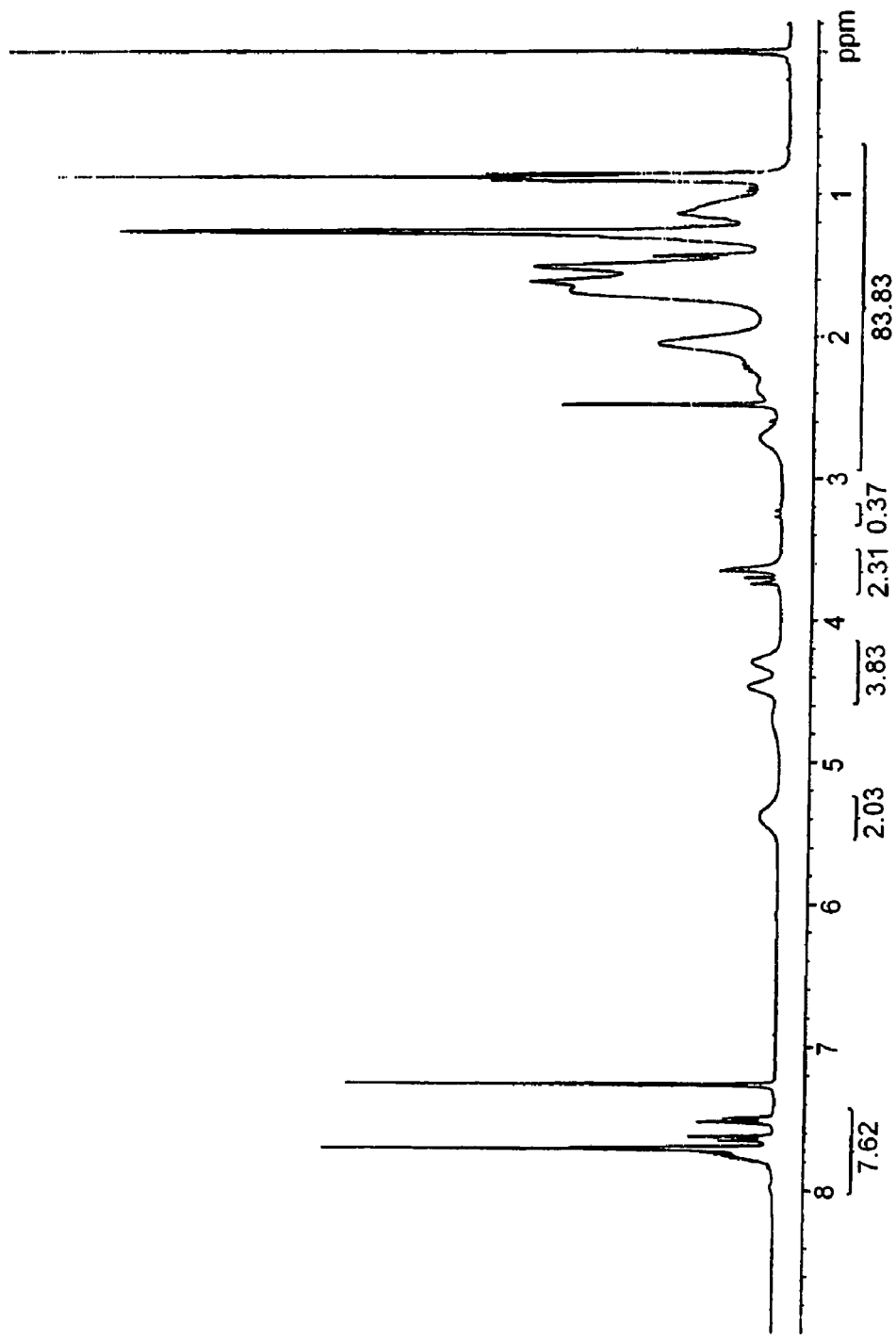
FIG. 4 shows the $^1$H-NMR spectrum of a compound according to another embodiment of the present invention.

The polystyrene-reduced weight average molecular weight (Mw) of this polymer was 1,230, and the molecular weight distribution (ratio of the weight average molecular weight to the number average molecular weight, Mw/Mn) was 1.54. FIG. 4 shows the $^1$H-NMR spectrum of this polymer.

Synthesis Example 8

As the monomers for polymerization, 10.9 g of 2-methyl-2-adamantyl acrylate, 7.7 g of γ-butyrolactyl methacrylate, and 10 g of 2-methylacrylic acid-2,2-difluoro-2-sulfoethyl ester diphenylfluorophenylsulfonium salt were first dissolved in 65 g of 1,2-dichloroethane. Next, 23 g of bicyclo[2.2.1]hept-5-ene-2-propanoic acid β-hydroxy-1,1-dimethylethyl ester (hereinafter, referred to as BHP), 5 g of AIBN as a polymerization initiator, and 131 g of 1,2-dichloroethane as a polymerization solvent were placed in a 250-ml flask, and then the mixture was stirred for 1 hour at ambient temperature under a nitrogen gas stream. While maintaining the temperature of the reaction tank at 65° C., the dissolved monomers for polymerization were slowly added dropwise to the flask over 1 hour, and then the reaction was allowed to proceed for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 34 g (yield: 66%) of the polymer represented by formula (15).

Figure 5:
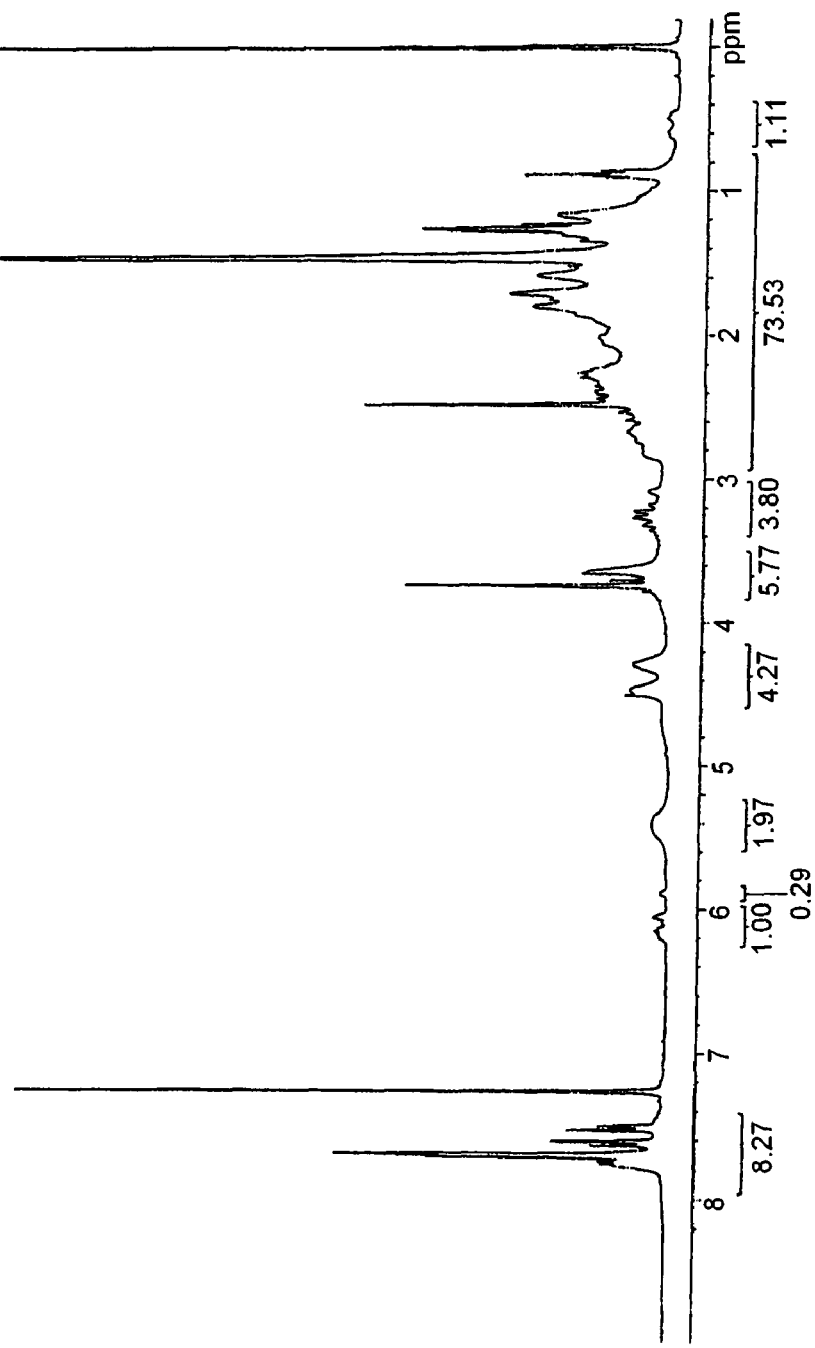
FIG. 5 shows the $^1$H-NMR spectrum of a compound according to another embodiment of the present invention.

The polystyrene-reduced weight average molecular weight (Mw) of this polymer was 1,210, and the molecular weight distribution (ratio of the weight average molecular weight to the number average molecular weight, Mw/Mn) was 1.3. FIG. 5 shows the $^1$H-NMR spectrum of this polymer.

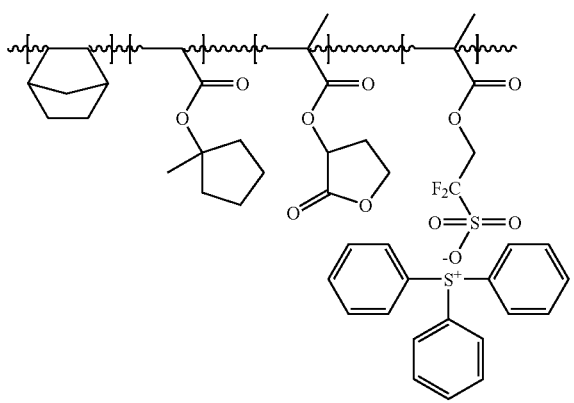

[Formula 14]

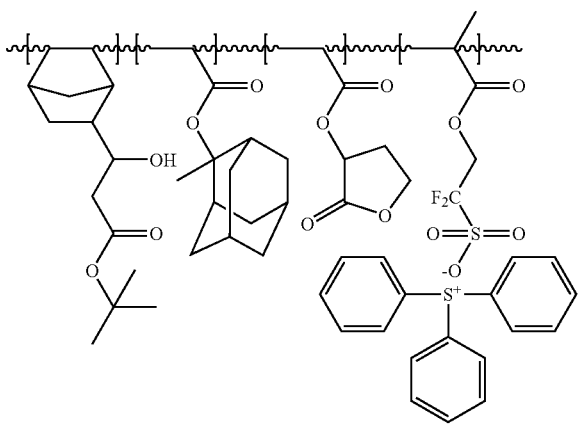

[Formula 15]

Synthesis Example 9

As the monomers for polymerization, 18.1 g of 2-isopropyladamantyl methacrylate, 10.0 g of γ-butyrolactyl methacrylate, 15 g of 3-hydroxy-1-adamantyl methacrylate, and 10 g of 2-methylacrylic acid-2,2-difluoro-2-sulfoethyl ester diphenylfluorophenylsulfonium salt were first dissolved in 74 g of 1,2-dichloroethane. Next, 5.6 g of norbornene, 6.4 g of AIBN as a polymerization initiator, and 148 g of 1,2-dichloroethane as a polymerization solvent were placed in a 250-ml flask, and then the mixture was stirred for 1 hour at ambient temperature under a nitrogen gas stream. While maintaining the temperature of the reaction tank at 65° C., the dissolved monomers for polymerization were slowly added dropwise to the flask over 1 hour, and then the reaction was allowed to proceed for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 52 g (yield: 88%) of the polymer represented by formula (16).

Figure 6:
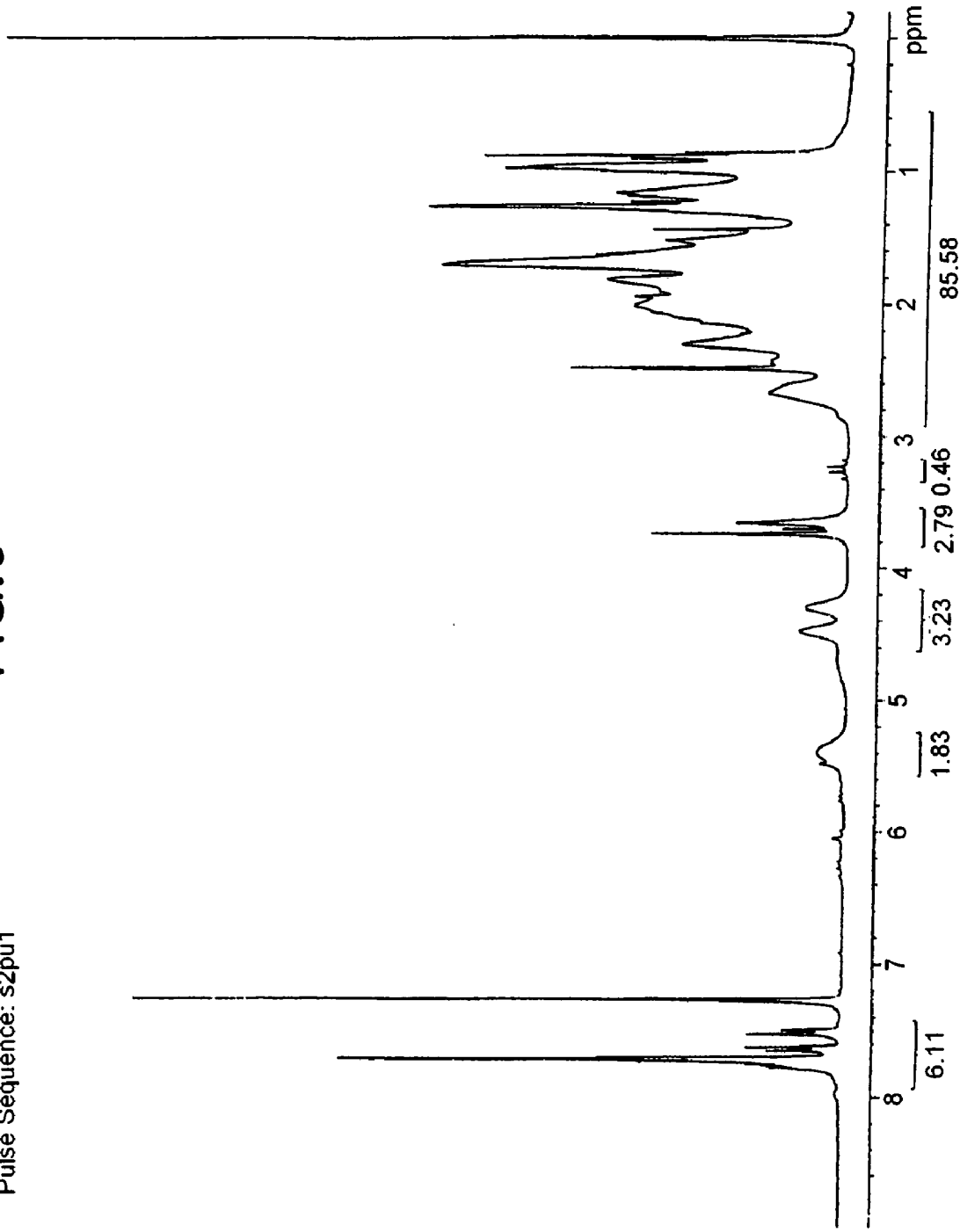
FIG. 6 shows the $^1$H-NMR spectrum of a compound according to another embodiment of the present invention.

The polystyrene-reduced weight average molecular weight (Mw) of this polymer was 1,160, and the molecular weight distribution (ratio of the weight average molecular weight to the number average molecular weight, Mw/Mn) was 1.57. FIG. 6 shows the $^1$H-NMR spectrum of this polymer.

Figure 7:
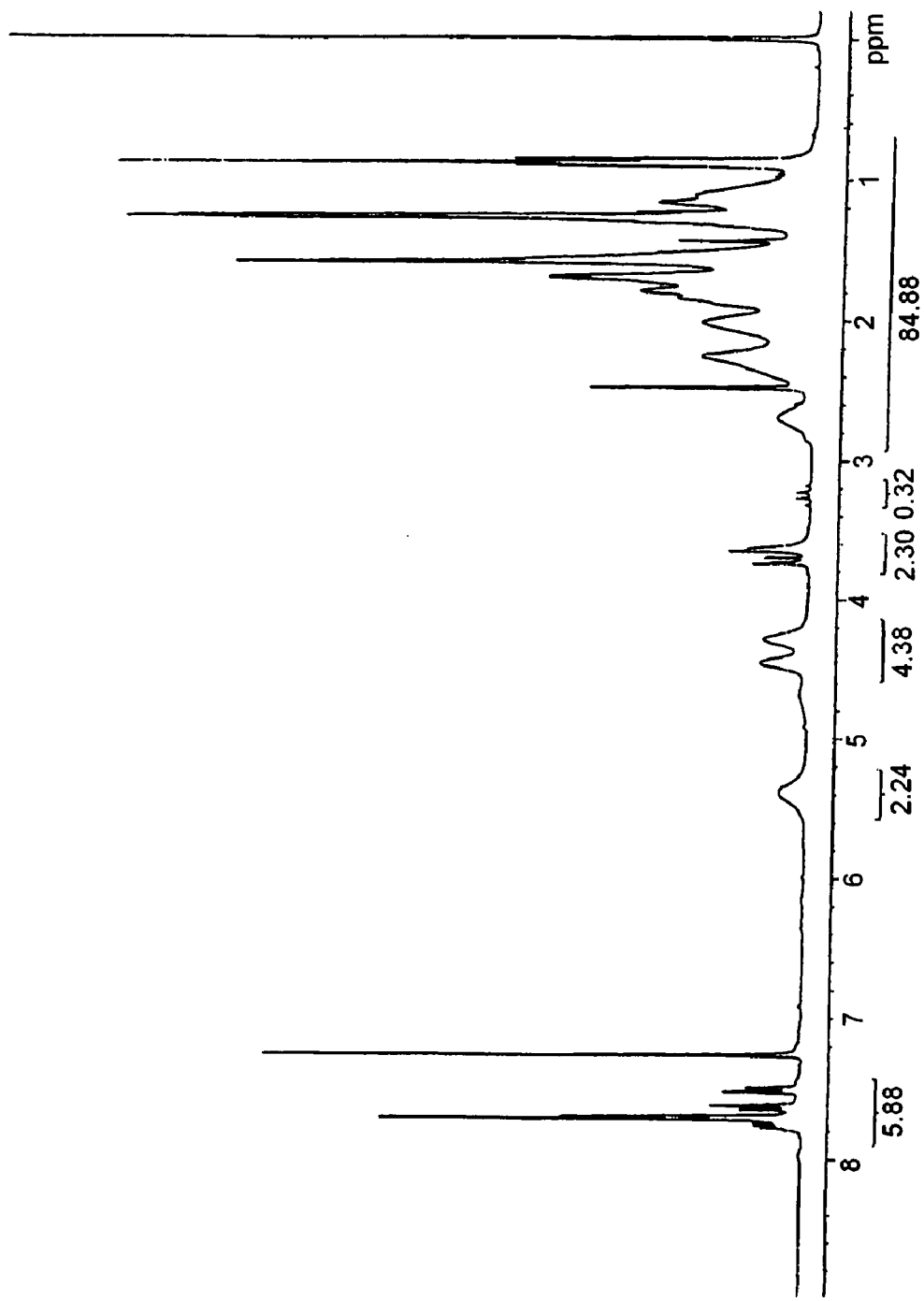
FIG. 7 shows the $^1$H-NMR spectrum of a compound according to another embodiment of the present invention.

The polystyrene-reduced weight average molecular weight (Mw) of this polymer was 1,280, and the molecular weight distribution (ratio of the weight average molecular weight to the number average molecular weight, Mw/Mn) was 1.58. FIG. 7 shows the $^1$H-NMR spectrum of this polymer.

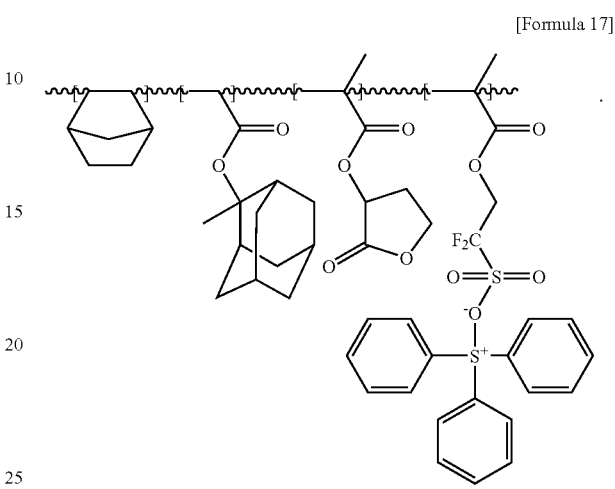

[Formula 17]

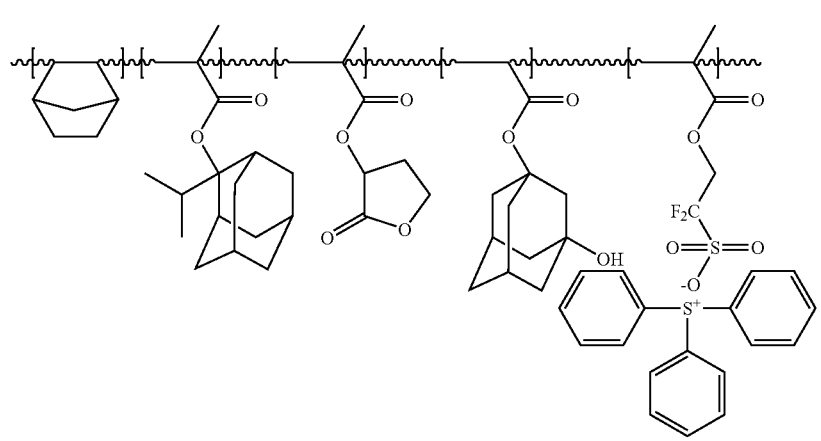

[Formula 16]

Synthesis Example 10

As the monomers for polymerization, 22 g of 2-methyl-2-adamantyl acrylate, 16.8 g of γ-butyrolactyl methacrylate, and 10 g of 2-methylacrylic acid-2,2-difluoro-2-sulfoethyl ester diphenylfluorophenylsulfonium salt were first dissolved in 68 g of 1,2-dichloroethane. Next, 5.6 g of norbornene, 6.4 g of AIBN as a polymerization initiator, and 136 g of 1,2-dichloroethane as a polymerization solvent were placed in a 250-ml flask, and then the mixture was stirred for 1 hour at ambient temperature under a nitrogen gas stream. While maintaining the temperature of the reaction tank at 65° C., the dissolved monomers for polymerization were slowly added dropwise to the flask over 1 hour, and then the reaction was allowed to proceed for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 54 g (yield: 90%) of the polymer represented by formula (17).

Synthesis Example 11

As the monomers for polymerization, 13.7 g of 2-methyl-2-cyclopentyl methacrylate, 10.1 g of γ-butyrolactyl methacrylate, 11.6 g of 3-hydroxy-1-adamantyl methacrylate, and 10 g of 2-methylacrylic acid-2,2-difluoro-2-sulfoethyl ester diphenylfluorophenylsulfonium salt were first dissolved in 64 g of 1,2-dichloroethane. Next, 5.6 g of norbornene, 6.4 g of AIBN as a polymerization initiator, and 128 g of 1,2-dichloroethane as a polymerization solvent were placed in a 250-ml flask, and then the mixture was stirred for 1 hour at ambient temperature under a nitrogen gas stream. While maintaining the temperature of the reaction tank at 65° C., the dissolved monomers for polymerization were slowly added dropwise to the flask over 1 hour, and then the reaction was allowed to proceed for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 53 g (yield: 92%) of the polymer represented by formula (18).

Figure 8:
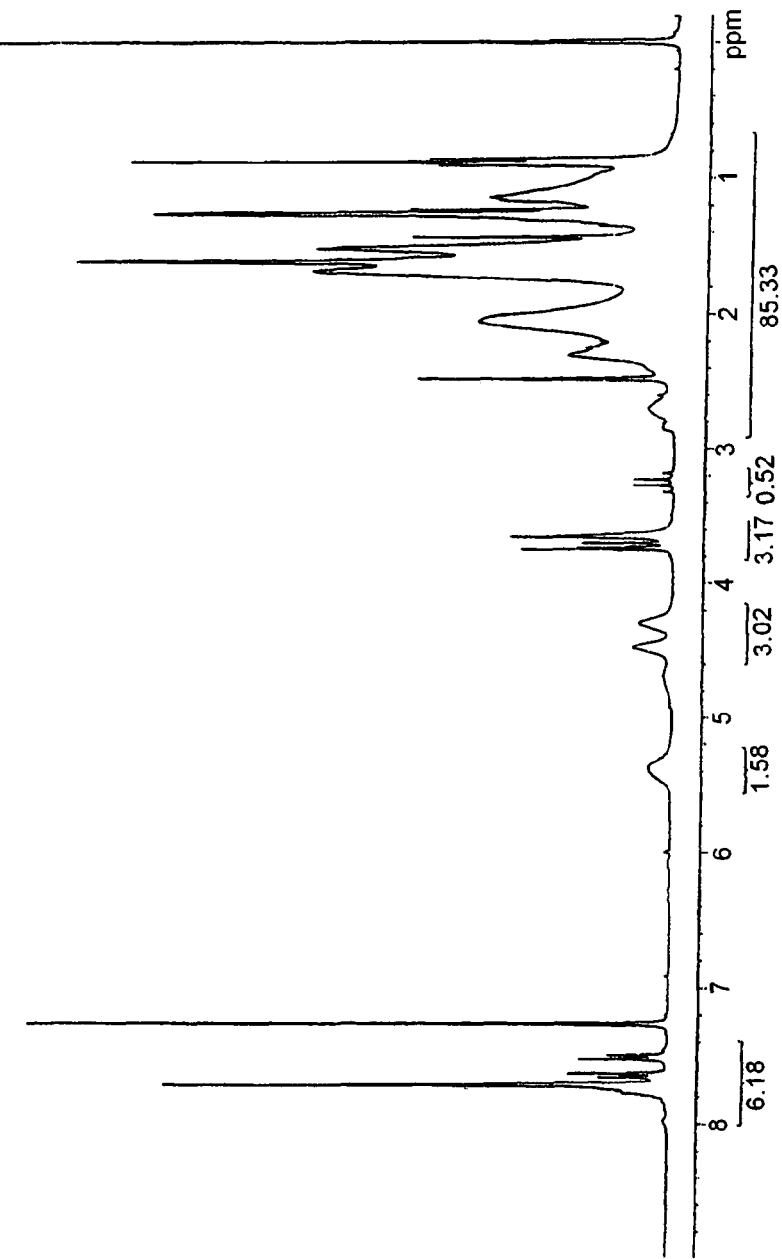
FIG. 8 shows the $^1$H-NMR spectrum of a compound according to another embodiment of the present invention.

The polystyrene-reduced weight average molecular weight (Mw) of this polymer was 1,380, and the molecular weight distribution (ratio of the weight average molecular weight to the number average molecular weight, Mw/Mn) was 1.57. FIG. 8 shows the $^1$H-NMR spectrum of this polymer.

<Preparation and Evaluation of Resist Composition>

Example 1

100 parts by weight of the polymer obtained in the Synthesis Example 6 (compound represented by formula (15)), 2.5 parts by weight of triphenylsulfonium nonaflate as an acid generator, and 0.75 parts by weight of tetramethylammonium

[Formula 18]

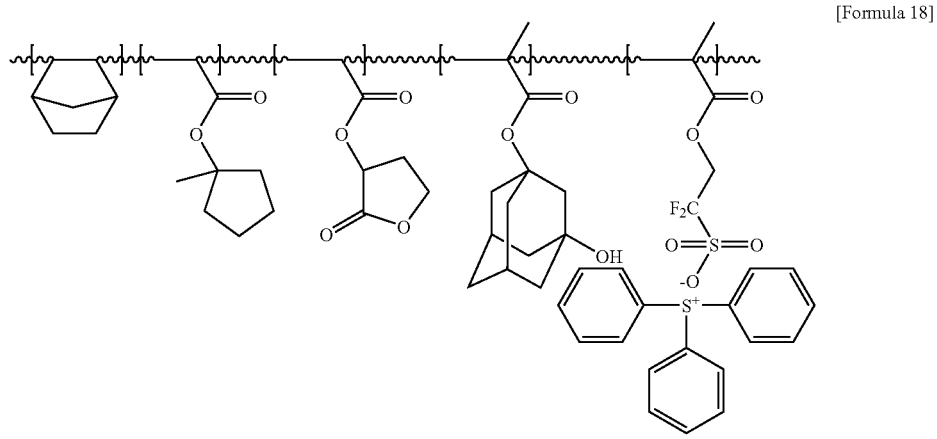

Comparative Synthesis Example 1

As the monomers for polymerization, 10.0 g of 2-methyl-2-adamantyl methacrylate, 7.3 g of γ-butyrolactyl methacrylate, and 10.1 g of 3-hydroxy-1-adamantyl methacrylate were mixed and dissolved in 82 g of 1,2-dioxane, and then the temperature of the reaction bath was slowly elevated to 65° C. While maintaining the temperature of the reaction at 65° C., the mixture was allowed to react for 16 hours. The solution obtained after the polymerization reaction was completed, was cooled to ambient temperature. The reaction solution cooled to ambient temperature was precipitated in hexane, and then the residues were filtered. Upon filtering, the residues were washed several times with the same solvent, and then dried under reduced pressure, to obtain 25 g (yield: 91%) of the polymer represented by formula (19).

Figure 9:
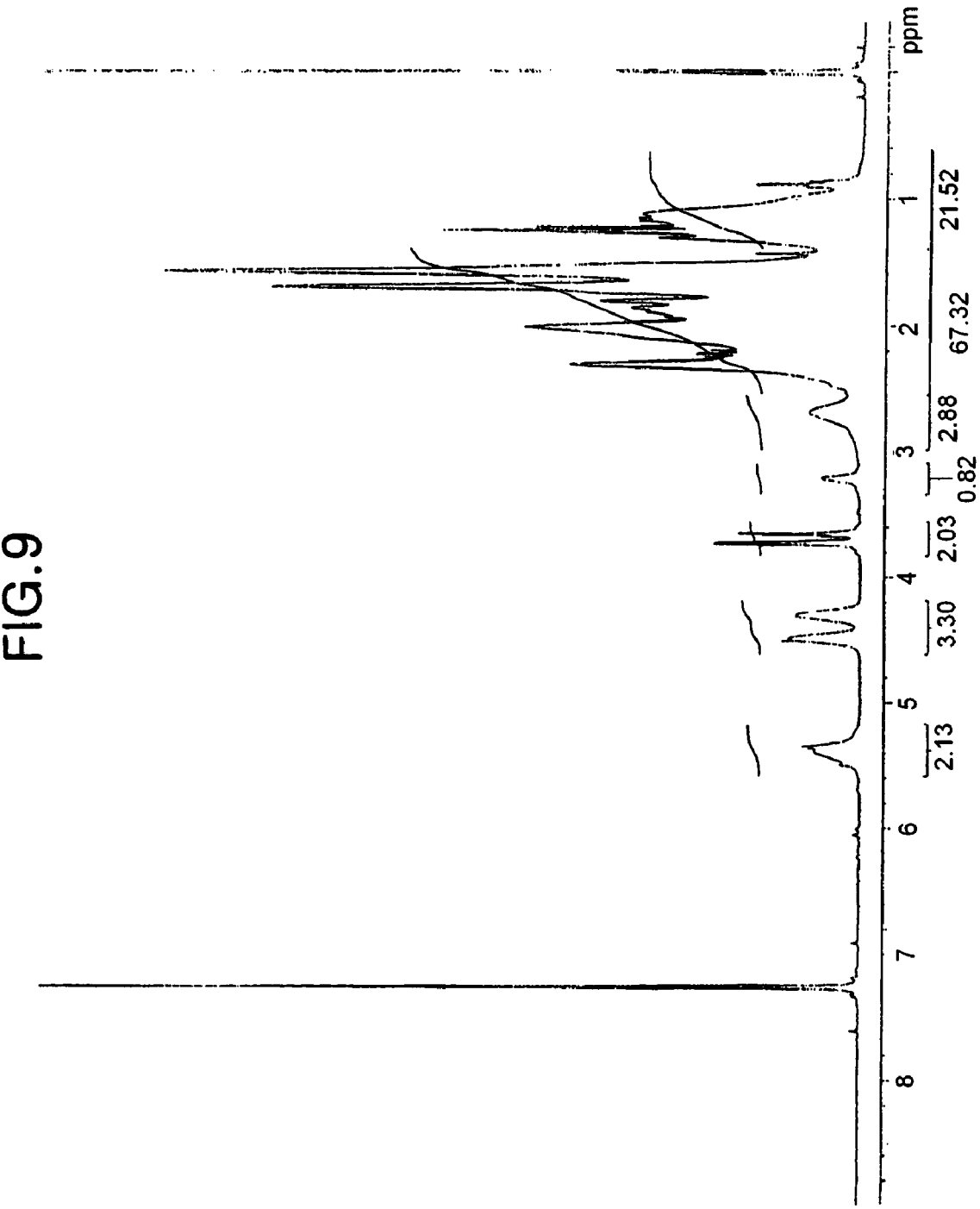
FIG. 9 shows the $^1$H-NMR spectrum of a compound according to another embodiment of the present invention.
Figure 10:
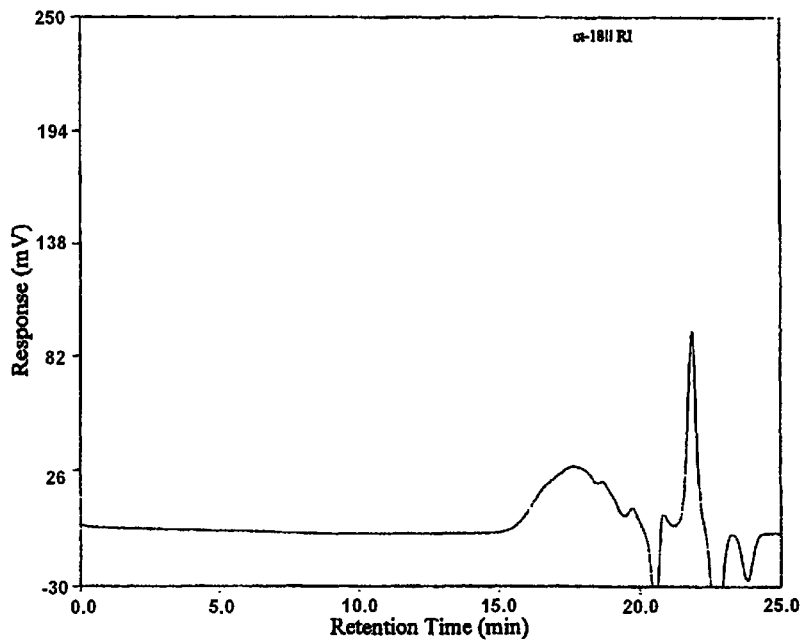
FIG. 10 shows the analytical data of gel permeation chromatography performed to measure the molecular weight of a compound according to another embodiment of the present invention.
Figure 11:
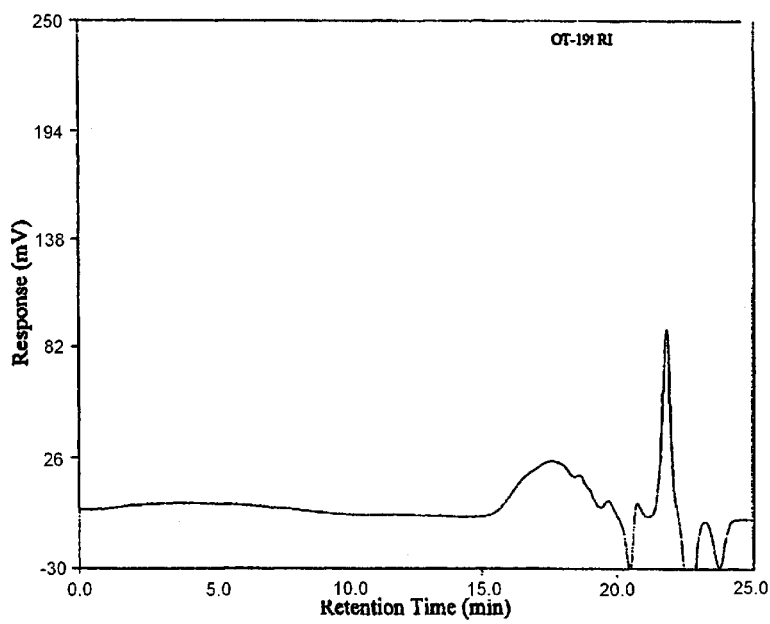
FIG. 11 shows the analytical data of gel permeation chromatography performed to measure the molecular weight of a compound according to another embodiment of the present invention.
Figure 12:
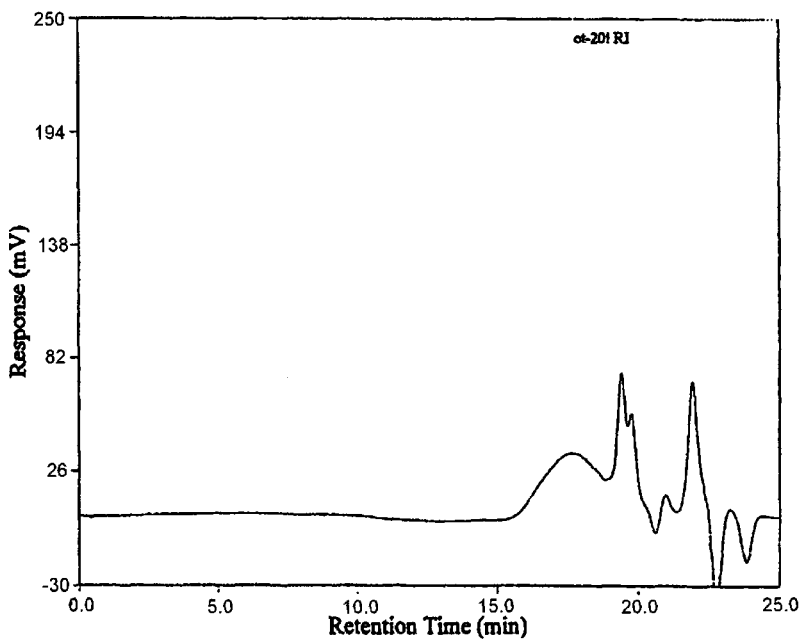
FIG. 12 shows the analytical data of gel permeation chromatography performed to measure the molecular weight of a compound according to another embodiment of the present invention.
Figure 13:
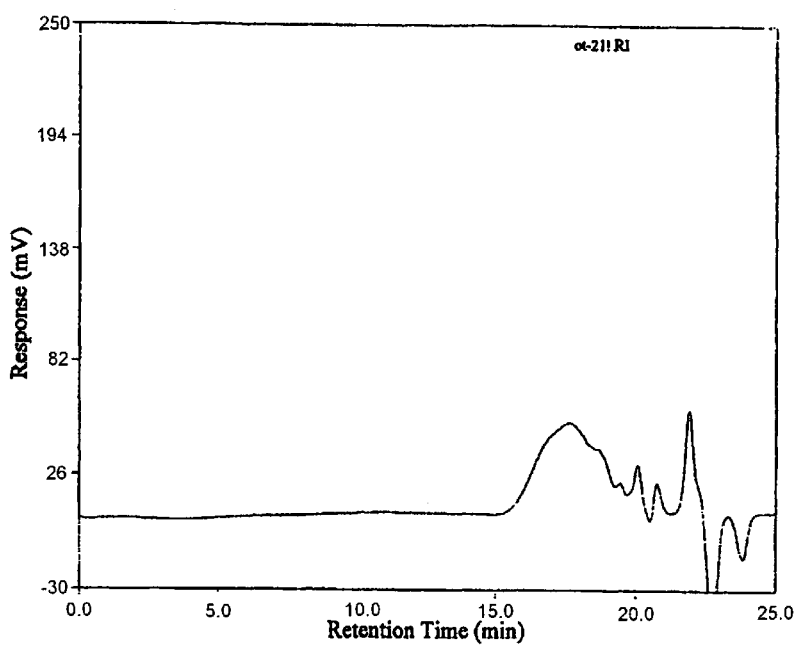
FIG. 13 shows the analytical data of gel permeation chromatography performed to measure the molecular weight of a compound according to another embodiment of the present invention.
Figure 14:
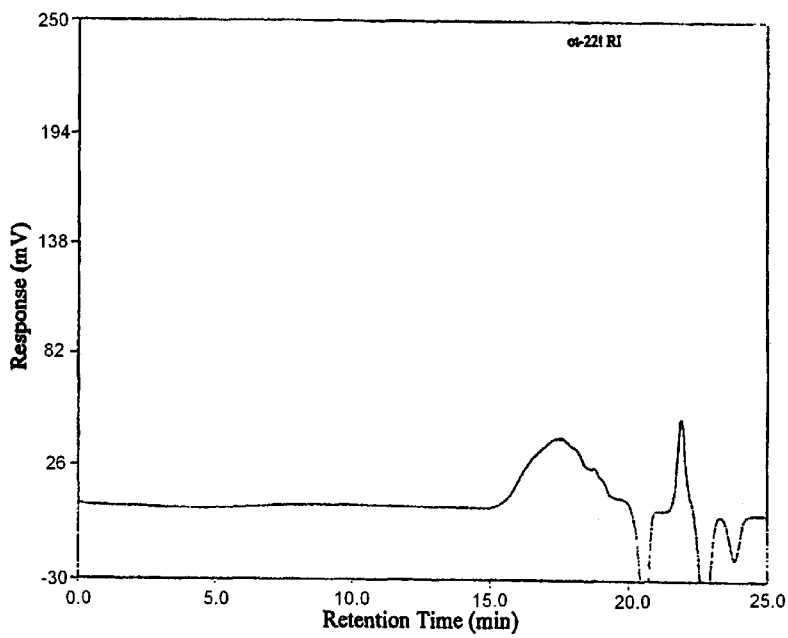
FIG. 14 shows the analytical data of gel permeation chromatography performed to measure the molecular weight of a compound according to another embodiment of the present invention.
Figure 15:
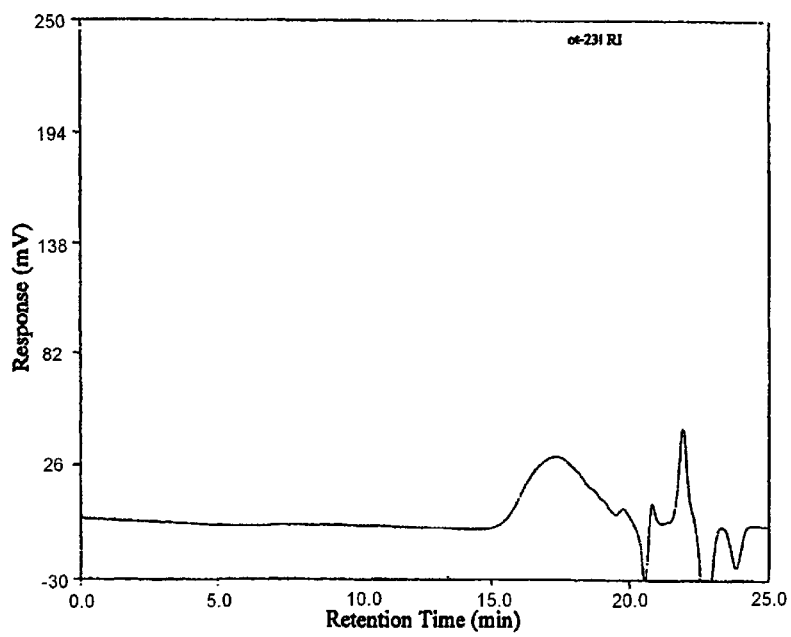
FIG. 15 shows the analytical data of gel permeation chromatography performed to measure the molecular weight of a compound according to another embodiment of the present invention.
Figure 16:
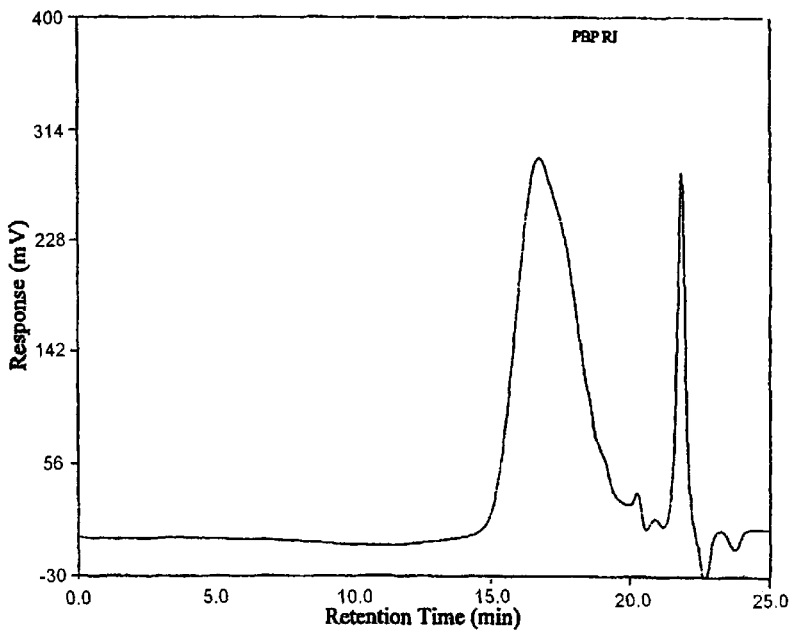
FIG. 16 shows the analytical data of gel permeation chromatography performed to measure the molecular weight of a compound according to another embodiment of the present invention.

The polystyrene-reduced weight average molecular weight (Mw) of this polymer was 1,780, and the molecular weight distribution (ratio of the weight average molecular weight to the number average molecular weight, Mw/Mn) was 1.68. FIG. 9 shows the $^1$H-NMR spectrum of this polymer.

[Formula 19]

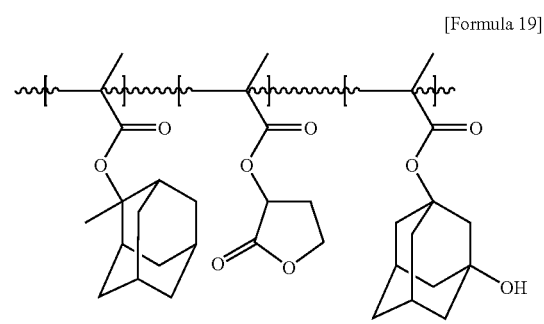

FIG. 10 to FIG. 16 show the analytical data of gel permeation chromatography performed to measure the molecular weights of the compounds of formula (13) to formula (19).

hydroxide as a basic additive were dissolved in 1,000 parts by weight of propylene glycol methyl ether acetate, and then the solution was filtered through a membrane filter having a pore size of 0.2 μm, to thus prepare a resist composition.

The obtained resist liquid was applied on a substrate using a spinner, and dried at 110° C. for 90 seconds, to form a film having a thickness of 0.2 μm. The formed film was exposed using an ArF excimer laser stepper (numerical aperture of lens: 0.75), and then the exposed film was heat treated at 120° C. for 90 seconds. Subsequently, the film was developed with a 2.38 wt % aqueous solution of tetramethylammonium hydroxide for 40 seconds, washed and dried to form a resist pattern.

The developability with the aqueous solution of tetramethylammonium hydroxide, and the adhesiveness of the formed resist pattern to the substrate were good, and the resolution was 0.08 μm, while the sensitivity was 13 mJ/cm$^2$.

The line edge roughness of the produced resist was measured by Critical Dimension-Scanning Electron Microscopy (CD-SEM), and the results were graded into 5 grades, such as 1 (very poor), 2 (poor), 3 (mediocre), 4 (good), and 5 (very good).

Furthermore, in the case of sensitivity, the amount of exposure which forms a 0.10-μm line-and-space (L/S) pattern formed after development at a line width of 1:1, was designated as the optimum amount of exposure, and this optimum amount of exposure was taken as the sensitivity. The minimum pattern dimension resolved at this time was designated as the resolution.

Examples 2 to 10

The resist compositions indicated in the following Table 1 were prepared in the same manner as in Example 1, except that the polymers obtained in the Synthesis Examples 7, 8 and 9 (compounds of formulas (16), (17) and (18)) were used instead of the polymer obtained in the Synthesis Example 6 (compound represented by formula (15)), and then positive resist patterns were formed therefrom. Evaluations of various properties were performed, and the results are presented in Table 1.

TABLE 1

| Content (parts by weight) | Polymer | Basic additive (2) | Sensitivity (mJ/cm$^2$) | Resolution (nm) | LER |
|---|---|---|---|---|---|
| Example 2 | Formula 15 (100) | 0.75 | 15 | 90 | 4 |
| Example 3 | Formula 17 (100) | 0.75 | 13 | 100 | 3 |
| Example 4 | Formula 18 (100) | 0.75 | 13.5 | 90 | 5 |
| Example 5 | Formula 15 (100) | 0.75 | 13 | 90 | 4 |
| Example 6 | Formula 17 (100) | 0.75 | 11 | 80 | 4 |
| Example 7 | Formula 18 (100) | 0.75 | 11 | 90 | 5 |
| Example 8 | Formula 15 (100) | 1 | 15.5 | 90 | 3 |
| Example 9 | Formula 17 (100) | 1 | 15 | 100 | 5 |
| Example 10 | Formula 18 (100) | 1 | 14 | 80 | 4 |

Remarks:
(1) Acid generator: Triphenylsulfonium nonaflate (PAG)
(2) Basic additive: Tetramethylammonium hydroxide As can be seen from the results of the Table 1, the line edge roughness and developability of the respective resist patterns obtained in the Examples were excellent.

Comparative Examples 1 to 3

Resist compositions were prepared using the compositions indicated in the following Table 2 in the same manner as in Example 1, except that a pure methacrylate polymer which is the compound represented by formula (19), synthesized in the Comparative Synthesis Example, was used as the polymer.

The respectively obtained composition solutions were used to form positive resist patterns in the same manner as in Example 1, using an ArF excimer laser exposure apparatus (numerical aperture of lens: 0.75), and then evaluations of various properties were performed. The results are presented in the following Table 2.

TABLE 2

| Content (parts by weight) | Polymer | Acid generator (1) | Basic additive (2) | Sensitivity (mJ/cm$^2$) | Resolution (µm) | LER |
|---|---|---|---|---|---|---|
| Comparative Example 1 | Formula 19 (100) | 2.5 | 0.75 | 16 | 90 | 2 |
| Comparative Example 2 | Formula 19 (100) | 3.0 | 0.75 | 15 | 80 | 1 |
| Comparative Example 3 | Formula 19 (100) | 3.0 | 1 | 16 | 90 | 2 |

Remarks:
(1) Acid generator: Triphenylsulfonium nonaflate (PAG)
(2) Basic additive: Tetramethylammonium hydroxide As can be seen from the results of the Table 2, when the Comparative Examples were evaluated and compared with the results of Table 1, the resolution was markedly lowered, and the line edge roughness viewed from the L/S patterns was significantly insufficient.

What is claimed is:
1. A polymer compound comprising a repeating unit represented by the following formula (5), a repeating unit represented by the following formula (6), and a repeating unit represented by the following formula (7):

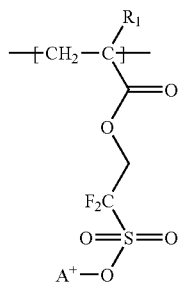

[Formula 5]

wherein $R_1$ represents a hydrogen atom, a trifluoromethyl group, an alkyl group having 1 to 5 carbon atoms, or an alkoxy group having 1 to 5 carbon atoms; and A represents a group represented by the following formula (2) or formula (3):

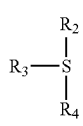

[Formula 2]

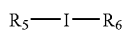

[Formula 3]

wherein $R_2$, $R_3$, $R_4$, $R_5$ and $R_6$ each independently represent a substituted or unsubstituted alkyl group having 1 to 20 carbon atoms, a substituted or unsubstituted allyl group having 3 to 10 carbon atoms, a substituted or unsubstituted perfluoroalkyl group having 1 to 10 carbon atoms, a substituted or unsubstituted benzyl group, or a substituted or unsubstituted aryl group having 6 to 30 carbon atoms; and two or more of $R_2$, $R_3$ and $R_4$ may be linked to each other to form a saturated or unsaturated carbon ring or a saturated or unsaturated heterocyclic ring;

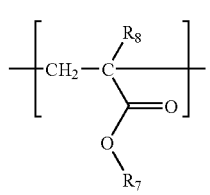

[Formula 6]

wherein $R_7$ represents a hydrogen atom, an alkyl group having 1 to 30 carbon atoms, or an alkyl group having 1 to 30 carbon atoms which is substituted with a group selected from an ether group, an ester group, a carbonyl group, an acetal group, an epoxy group, a nitrile group and an aldehyde group; and $R_8$ represents a hydrogen atom, a methyl group, or a trifluoromethyl group;

[Formula 7]

$$-\!\!\{\!X\!\}\!\!-$$

wherein X represents one selected from olefin, vinyl, styrene, and derivatives thereof.

2. The polymer compound according to claim 1, wherein the polymer compound comprises three different species of the repeating unit represented by formula (6).

3. The polymer compound according to claim 2, wherein when the polymer compound comprising three different species of the repeating unit represented by formula (6) is represented by the following formula (8), the polymer compound is represented by any one of the formulas of formula (9):

[Formula 8]

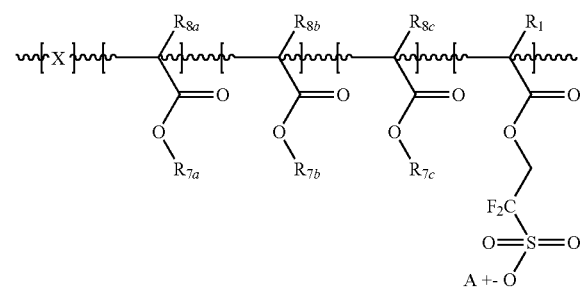

wherein $R_1$ represents a hydrogen atom, a trifluoromethyl group, an alkyl group having 1 to 5 carbon atoms, or an alkoxy group having 1 to 5 carbon atoms; $R_{7a}$, $R_{7b}$ and $R_{7c}$ each independently represent a hydrogen atom, a linear or branched alkyl group having 1 to 30 carbon atoms, or a linear or branched alkyl group having 1 to 30 carbon atoms which is substituted with an ether group, an ester group, a carbonyl group, an acetal group, an epoxy group, a nitrile group or an aldehyde group; $R_{8a}$, $R_{8b}$ and $R_{8c}$ each independently represent a hydrogen atom, a methyl group or a trifluoromethyl group; and A represents a group represented by the following formula (2) or formula (3):

[Formula 2]

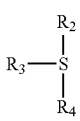

[Formula 3]

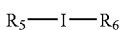

wherein $R_2$, $R_3$, $R_4$, $R_5$ and $R_6$ each independently represent a substituted or unsubstituted alkyl group having 1 to 20 carbon atoms, a substituted or unsubstituted allyl group having 3 to 10 carbon atoms, a substituted or unsubstituted perfluoroalkyl group having 1 to 10 carbon atoms, a substituted or unsubstituted benzyl group, or a substituted or unsubstituted aryl group having 6 to 30 carbon atoms; and two or more of $R_2$, $R_3$ and $R_4$ may be linked to each other to form a saturated or unsaturated carbon ring or a saturated or unsaturated heterocyclic ring;

[Formula 9]

[Formula 9-a]

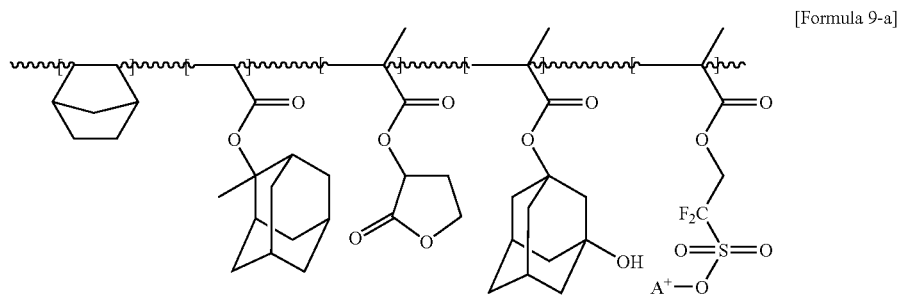

[Formula 9-b]

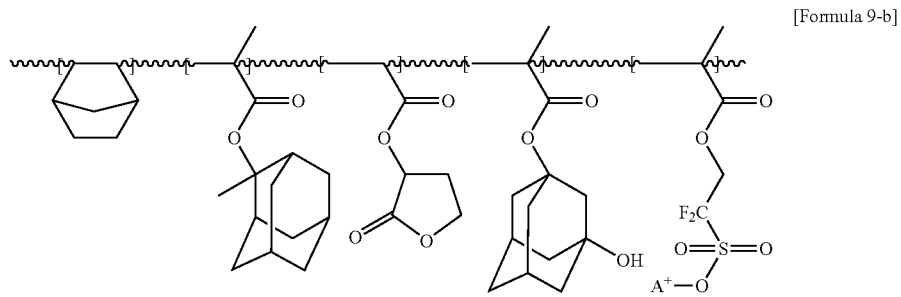

[Formula 9-c]
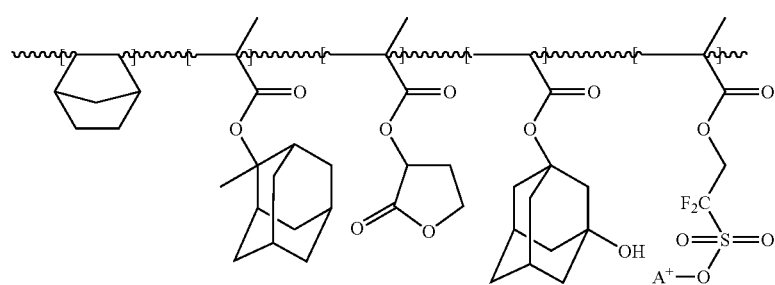
[Formula 9-d]
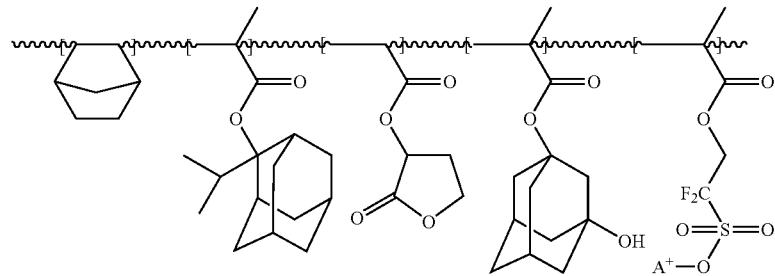
[Formula 9-e]
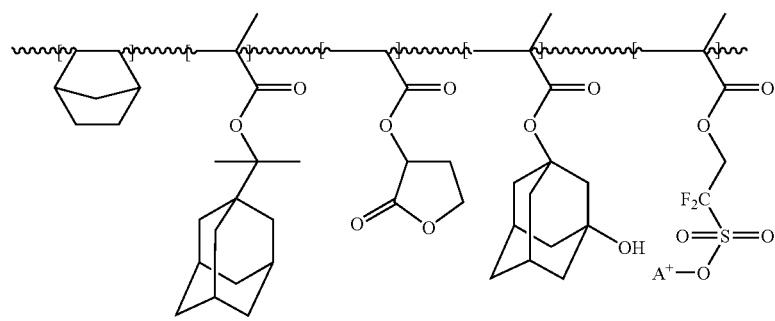
[Formula 9-f]
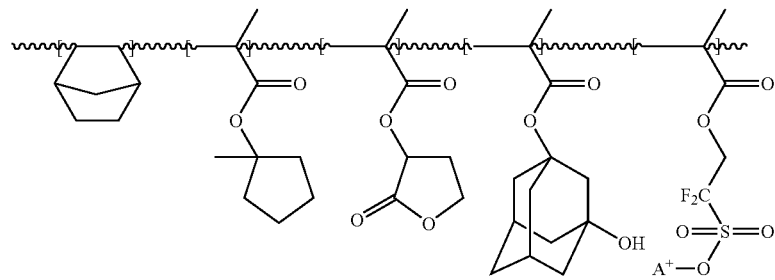
[Formula 9-g]
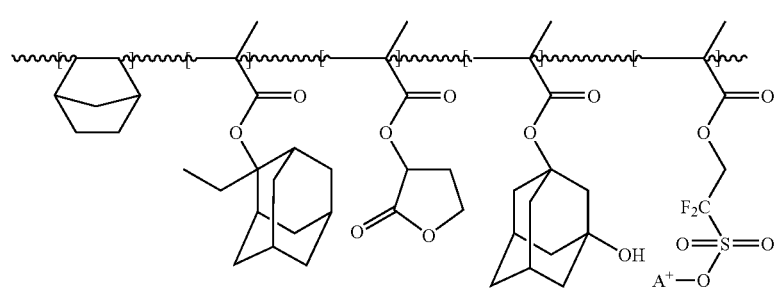

[Formula 9-h]
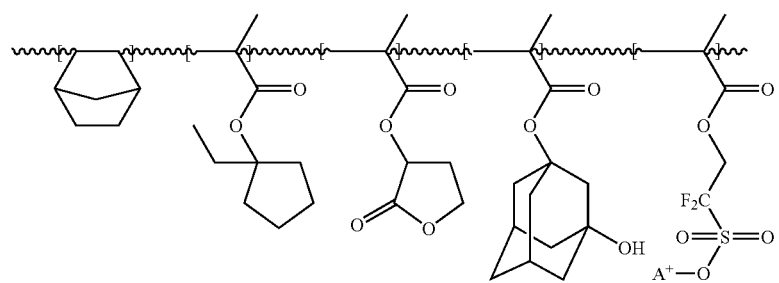
[Formula 9-i]
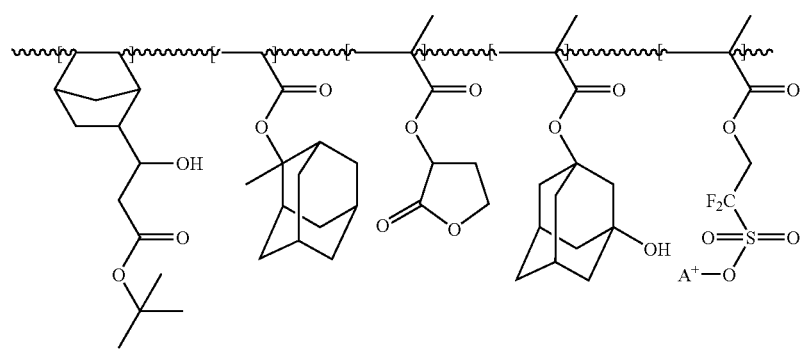
[Formula 9-j]
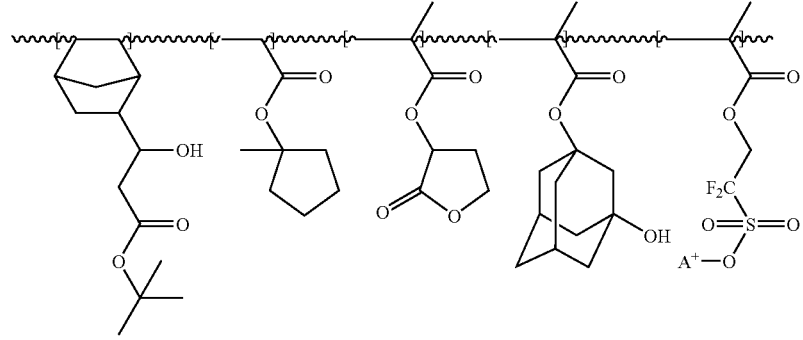
[Formula 9-k]
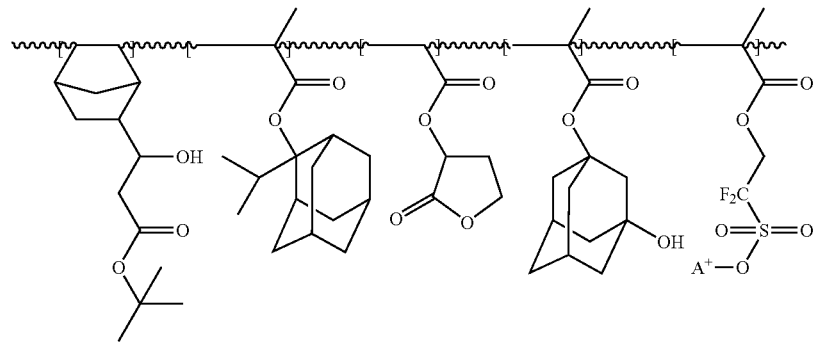

[Formula 9-1]
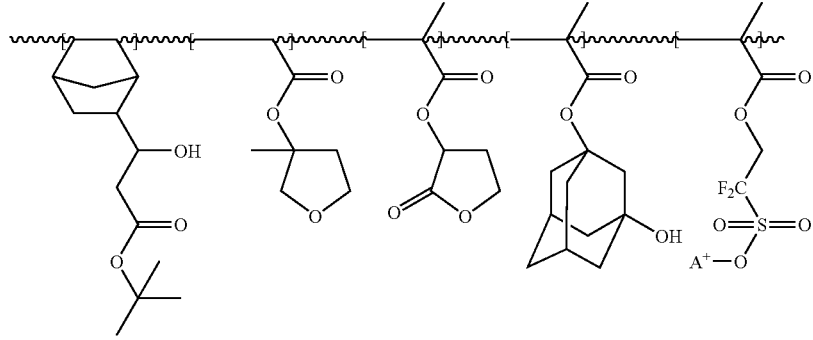
4. The polymer compound according to claim 1, wherein A is represented by one of the following formulas of formula (4):
[Formula 4]
[Formula 4-a]
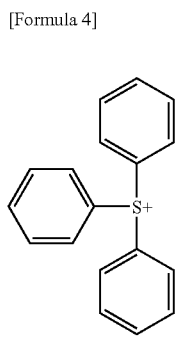
[Formula 4-b]
[Formula 4-c]
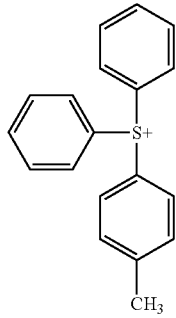
[Formula 4-d]
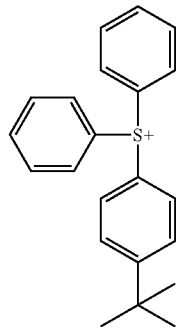
[Formula 4-e]
[Formula 4-f]

[Formula 4-g]
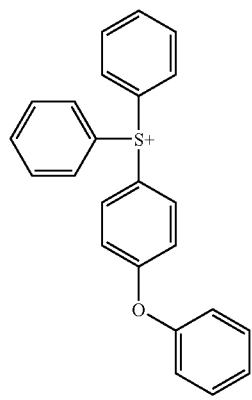
[Formula 4-h]
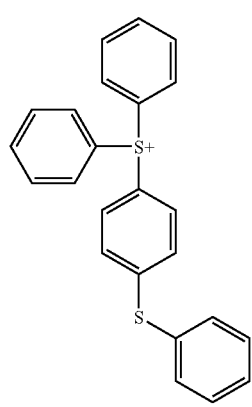
[Formula 4-i]
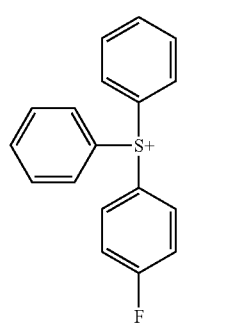
[Formula 4-j]
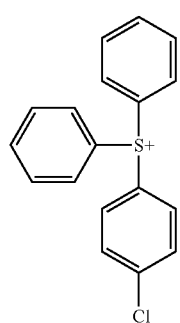
[Formula 4-k]
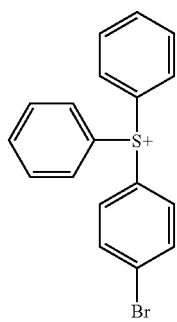
[Formula 4-l]
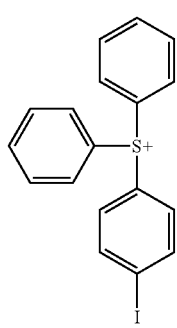
[Formula 4-m]
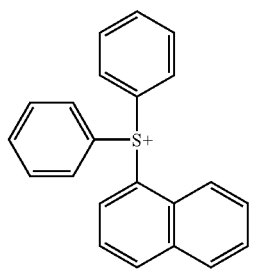
[Formula 4-n]
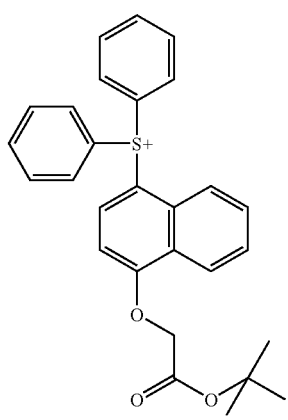
[Formula 4-o]
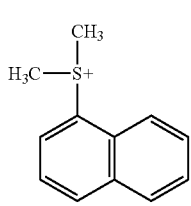

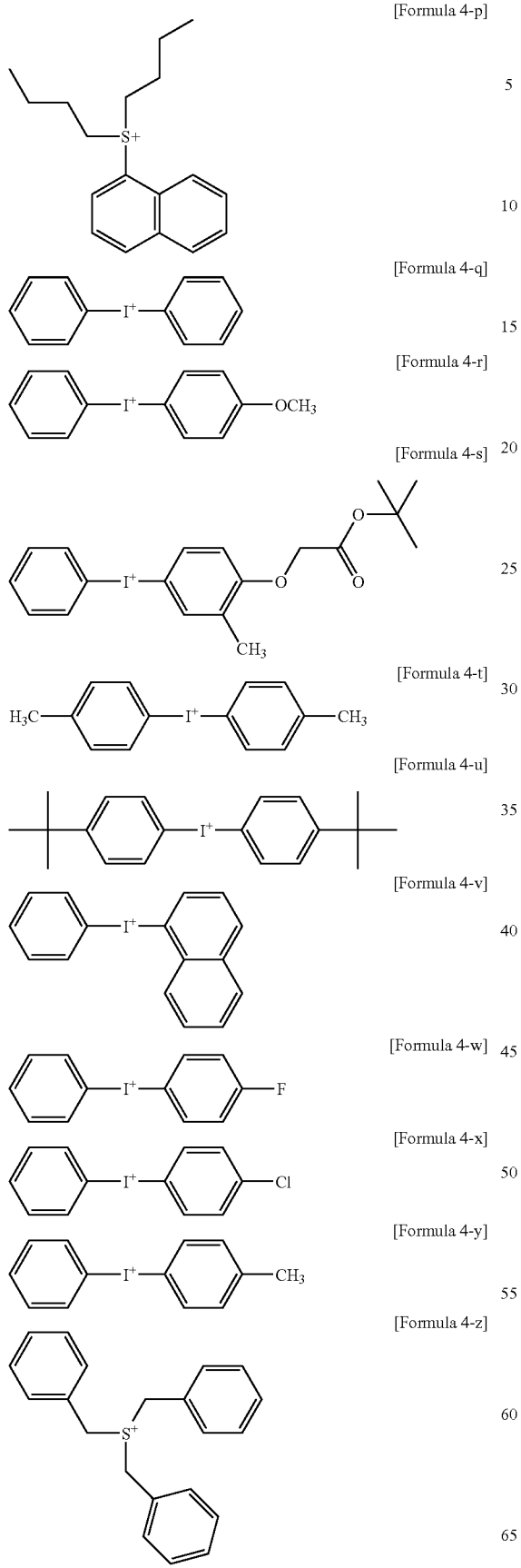
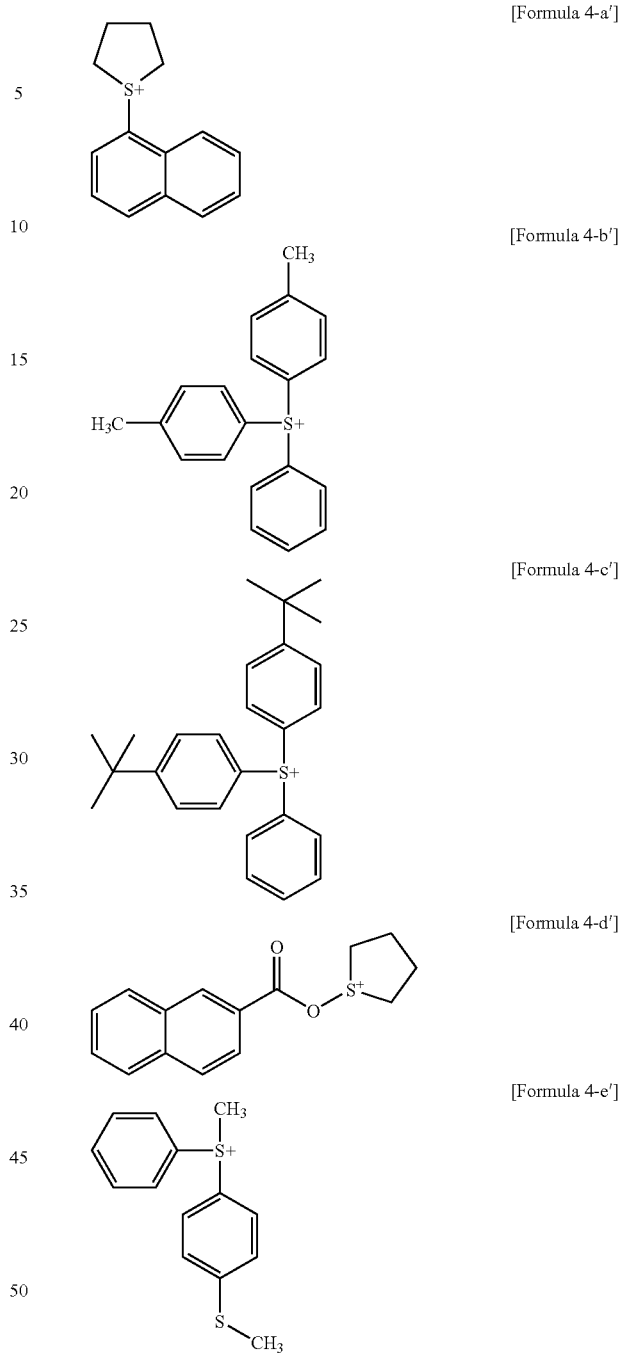

5. The polymer compound according to claim 1, further comprising a repeating unit having an acid-labile group, and a repeating unit having a hydroxyl group, a lactone ring group, or both a hydroxyl group and a lactone ring group.

6. A chemically amplified resist composition comprising the polymer compound according to claim 1, an acid generator, additives, and a solvent.

7. The chemically amplified resist composition according to claim 6, wherein the content of the moiety $-(SO_3)^-(A)^+$ in the polymer compound is 0.5 parts by weight to 15 parts by weight based on 100 parts by weight of the total solid fraction of the chemically amplified resist composition.

8. The chemically amplified resist composition according to claim 6, wherein the content of the polymer compound is 3% by weight or more based on the chemically amplified resist composition.

9. The chemically amplified resist composition according to claim 6, wherein the content of the polymer compound is 5% by weight based on the chemically amplified resist composition.

10. A method for forming a pattern, the method comprising:
   (a) applying the chemically amplified resist composition according to claim 6 on a substrate;
   (b) heat treating the substrate coated with the chemically amplified resist composition, and then exposing the substrate with high energy radiation; and
   (c) developing the outcome from the step (b) using a developer solution.

11. The method according to claim 10, wherein the exposing the substrate with high energy radiation employs ultraviolet irradiation, X-ray irradiation, or an electron beam irradiation.

12. The method according to claim 10, wherein the wavelength of the high energy radiation is in the range of 180 nm to 250 nm.

13. A chemically amplified resist composition comprising the polymer compound according to claim 2, an acid generator, additives, and a solvent.

14. A chemically amplified resist composition comprising the polymer compound according to claim 3, an acid generator, additives, and a solvent.

15. A chemically amplified resist composition comprising the polymer compound according to claim 4, an acid generator, additives, and a solvent.

16. A chemically amplified resist composition comprising the polymer compound according to claim 5, an acid generator, additives, and a solvent.

* * * * *